(12) United States Patent
Halbert et al.

(10) Patent No.: US 6,670,452 B2
(45) Date of Patent: *Dec. 30, 2003

(54) NON-NATURALLY OCCURRING LIPOPROTEIN PARTICLE

(75) Inventors: Gavin William Halbert, Jordanhill (GB); Moira Doreen Owens, Shawlands (GB); George Baillie, Kilmarnock (GB)

(73) Assignee: University of Strathclyde, Glasgow (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/269,533

(22) PCT Filed: Sep. 25, 1997

(86) PCT No.: PCT/GB97/02610
§ 371 (c)(1),
(2), (4) Date: Jun. 1, 1999

(87) PCT Pub. No.: WO98/13385
PCT Pub. Date: Feb. 4, 1998

(65) Prior Publication Data
US 2002/0147304 A1 Oct. 10, 2002

(30) Foreign Application Priority Data
Sep. 27, 1996 (GB) ................................ 9620153

(51) Int. Cl.[7] ................................ C07K 1/00

(52) U.S. Cl. ........................ 530/359; 530/350; 435/7.1; 536/23.5

(58) Field of Search ................................ 530/350, 359; 536/23.5; 435/7.1

(56) References Cited

FOREIGN PATENT DOCUMENTS

| WO | WO 87/02061 | * | 4/1987 |
| WO | 92/21330 | | 12/1992 |

OTHER PUBLICATIONS

Lundberg et al. Conjugation of apolipoprotein B with liposomes and targeting to cells in culture. Biochim. Biophys. Acta (1993) 1149: 305–312.*

M.D. Owens, Gavin W. Halbert, "Production and Charactereization of Protein–free Analogues of Low Density Lipoprotein", Sep. 19, 1994, pp. 20–26, European Journal of Pharmaceutics and Biopharmaceutics, Stuttgart, DE, No. 2.

G.W. Halbert, M.D. Owens and G.S. Baillie, "Interaction of Amphiphatic Aproprotein B Receptor Peptides with Microemulsions", pp. 797–798, Department of Pharmaceutical Sciences, Strathclyde University, Glasgow, G1 1XW, UK.

* cited by examiner

Primary Examiner—Christopher S. F. Low
Assistant Examiner—Hope A. Robinson
(74) Attorney, Agent, or Firm—Alston & Bird LLP

(57) ABSTRACT

Non-naturally occurring receptor competent LDL particle comprising at least one peptide component wherein the said peptide component comprises at least a binding site for an Apo B protein receptor and at least one lipophilic substituent.

12 Claims, 16 Drawing Sheets

Figure 1:
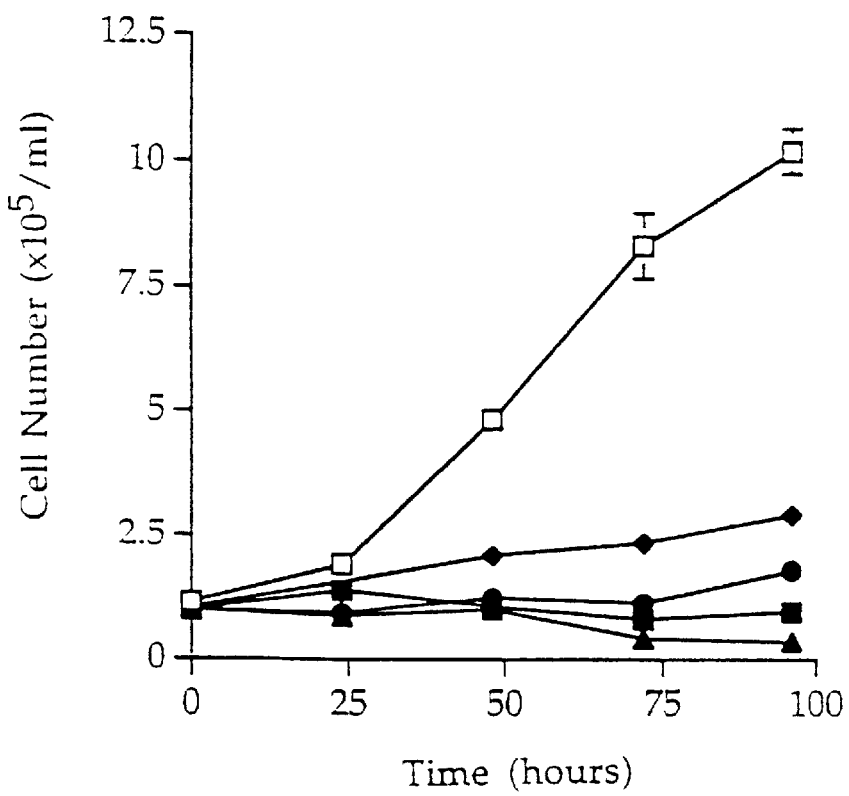

Me  Microemulsion Control
A   Peptide A-nLDL
B   Peptide B-nLDL
C   Peptide C-nLDL
D   Peptide D-nLDL
E   Peptide E-nLDL Peptide A    Retinoic    —    Leu-Arg-Leu-Thr-Arg-Lys-Arg-Gly-Leu-Lys-Leu-Cholesterol
             Acid Peptide B    Retinoic    —    Gly-Thr-Thr-Arg-Leu-Thr-Arg-Lys-Arg-Gly-Leu-Lys-Leu-OH
             Acid Peptide C    Retinoic    —    Tyr-Lys-Leu-Glu-Gly-Thr-Thr-Arg-Leu-Thr-Arg-Lys-Arg-Gly-Leu-Lys-
             Acid             Leu-Ala-Thr-Ala-Leu-Ser-Cholesterol Peptide D    Retinoic    —    Tyr-Lys-Leu-Glu-Gly-Thr-Thr-Arg-Leu-Thr-Arg-Lys-Arg-Gly-Leu-Lys-
             Acid             Leu-Ala-Thr-Ala-Leu-Ser-OH Peptide E    Retinoic    —    Thr-Gly-Lys-Arg-Tyr-Arg-Leu-Lys-Thr-Leu-Arg-Thr-Leu-Lys-Lys-Thr-
             Acid             Ser-Leu-Glu-Ala-Ala-OH FIG. 7    Synthetic polypeptide analogues of the apo-B100 binding site (Peptides A-E inclusive)

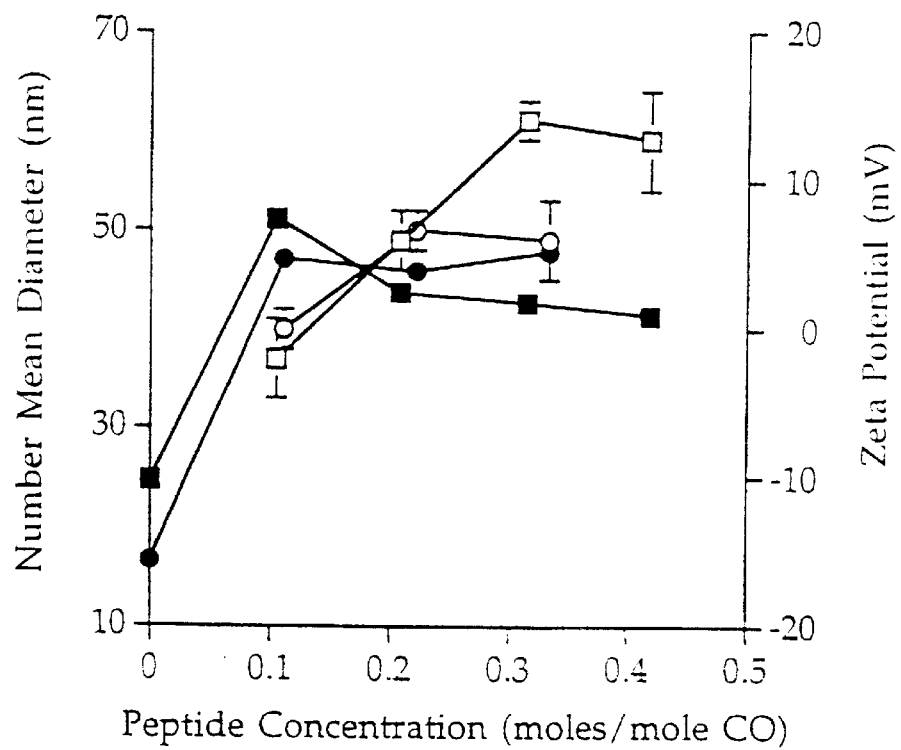
F I G. 10c
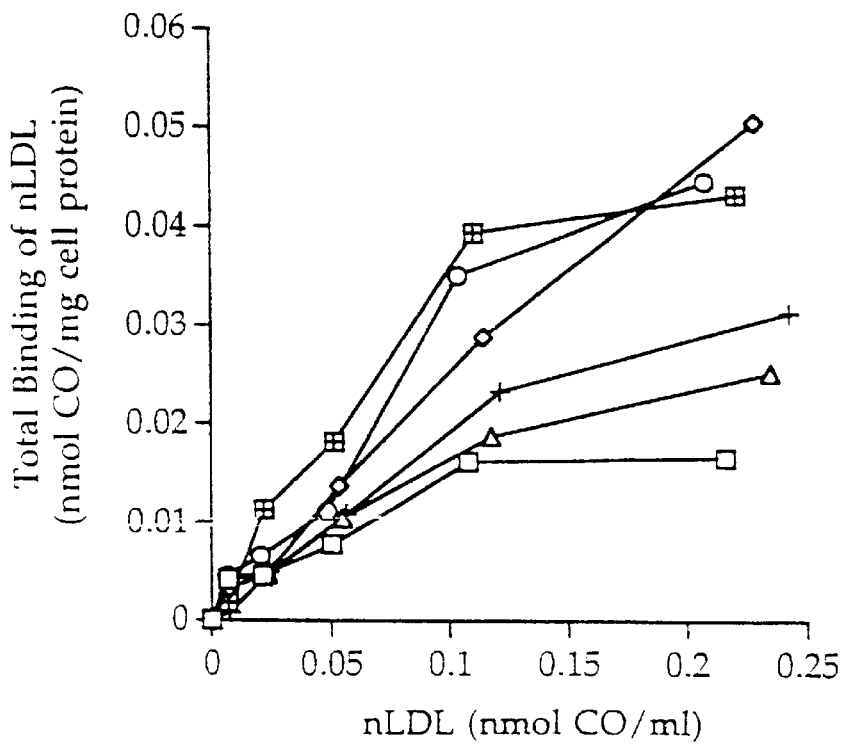
F I G. 11

SEQUENCE LISTING

```
<160> NUMBER OF SEQ ID NOS: 7

<210> SEQ ID NO 1
<211> LENGTH: 11
<212> TYPE: PRT
<213> ORGANISM: Artificial Sequence
<220> FEATURE:
<221> NAME/KEY: misc_feature
<222> LOCATION: ()..()
<223> OTHER INFORMATION: Apo B binding site sequence

<400> SEQUENCE: 1

Lys Ala Glu Tyr Lys Lys Asn Lys His Arg His
1               5                   10

<210> SEQ ID NO 2
<211> LENGTH: 11
<212> TYPE: PRT
<213> ORGANISM: Artificial Sequence
<220> FEATURE:
<221> NAME/KEY: misc_feature
<222> LOCATION: ()..()
<223> OTHER INFORMATION: Apo B binding site sequence

<400> SEQUENCE: 2

Thr Thr Arg Leu Thr Arg Lys Arg Gly Leu Lys
1               5                   10

<210> SEQ ID NO 3
<211> LENGTH: 11
<212> TYPE: PRT
<213> ORGANISM: Artificial Sequence
<220> FEATURE:
<221> NAME/KEY: misc_feature
<222> LOCATION: ()..()
```

```
<223> OTHER INFORMATION: Synthesised peptide analogue of the Apo B 100
      binding site
<221> NAME/KEY: misc_feature
<222> LOCATION: ()..()
<223> OTHER INFORMATION: Cholesterol linked at C-terminus of peptide
      analogue
<221> NAME/KEY: misc_feature
<222> LOCATION: ()..()
<223> OTHER INFORMATION: Retinoic acid linked at N-terminus of peptide
      analogue

<400> SEQUENCE: 3

Leu Arg Leu Thr Arg Lys Arg Gly Leu Lys Leu
1               5                   10

<210> SEQ ID NO 4
<211> LENGTH: 13
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthesised peptide analogue of the Apo B 100
      binding site
<221> NAME/KEY: misc_feature
<222> LOCATION: ()..()
<223> OTHER INFORMATION: Retinoic acid linked at N-terminus of peptide
      analogue

<400> SEQUENCE: 4

Gly Thr Thr Arg Leu Thr Arg Lys Arg Gly Leu Lys Leu
1               5                   10

<210> SEQ ID NO 5
<211> LENGTH: 22
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthesised peptide analogue of the Apo B 100
      binding site
<221> NAME/KEY: misc_feature
<222> LOCATION: ()..()
<223> OTHER INFORMATION: Cholesterol linked at C-terminus of peptide
      analogue
<221> NAME/KEY: misc_feature
<222> LOCATION: ()..()
<223> OTHER INFORMATION: Retinoic acid linked at N-terminus of peptide
      analogue

<400> SEQUENCE: 5

Tyr Lys Leu Gln Gly Thr Thr Arg Leu Thr Arg Lys Arg Gly Leu Lys
1               5                   10                  15

Leu Ala Thr Ala Leu Ser
            20

<210> SEQ ID NO 6
<211> LENGTH: 22
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthesised peptide analogue of the Apo B 100
      binding site
<221> NAME/KEY: misc_feature
<222> LOCATION: ()..()
<223> OTHER INFORMATION: Retinoic acid linked at N-terminus of peptide
      analogue

<400> SEQUENCE: 6
```

```
Tyr Lys Leu Glu Gly Thr Thr Arg Leu Thr Arg Lys Arg Gly Leu Lys
1               5                   10                  15

Leu Ala Thr Ala Leu Ser
                20

<210> SEQ ID NO 7
<211> LENGTH: 22
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthesised peptide analogue of the Apo B 100
      binding site
<221> NAME/KEY: misc_feature
<222> LOCATION: ()..()
<223> OTHER INFORMATION: Retinoic acid linked at N-terminus of peptide
      analogue

<400> SEQUENCE: 7

Thr Gly Lys Arg Tyr Arg Leu Lys Thr Leu Arg Thr Leu Lys Lys Thr
1               5                   10                  15

Ser Leu Leu Glu Ala Ala
                20
```

NON-NATURALLY OCCURRING LIPOPROTEIN PARTICLE

BACKGROUND

The present invention relates to lipoprotein particles, a process for preparing such particles and their use. In particular, the invention relates to non-naturally occurring low density lipoprotein particles, methods for their manufacture and use thereof.

Low density lipoprotein (LDL) is a natural component of plasma which is involved in the transport of cholesterol in the form of cholesterol esters around the body. Naturally occurring LDL is known to occur as roughly spherical-shaped particles (20–22 nm in diameter) which comprise an internal core of about 1500 cholesterol esters containing small amounts of triglyceride (TG). The internal core is typically surrounded by a solubilising monolayer of about 800 phospholipid molecules and small quantities of free cholesterol (about 500 molecules). Located in the monolayer is a large receptor protein, Apo protein B, of approx 500,000 daltons, (Apo B) which accounts for about twenty percent of the weight of the LDL particle.

Naturally occurring LDL finds use in a number of areas, for example, in studies on atherosclerosis and lipid metabolism. LDL also finds use as a drug-targeting vector in cancer chemotherapy. Certain cancerous cells display high rates of receptor mediated LDL uptake relative to normal cells and as such, LDL has also found use as a targeting vector for anti-cancer drugs.

Currently, naturally occurring LDL needs to be isolated from fresh plasma samples. The isolation procedure is lengthy (e.g. up to 48 hours) and depending on the donor's plasma LDL levels the yield of LDL can be any amount up to about 100 mg ApoB/100 ml plasma in healthy individuals. Thus, yields are generally low.

Isolated naturally occurring LDL is known to be unstable. Attempts have been made to produce LDL-like particles, generally in the form of microemulsions of similar size and lipid composition to naturally occurring LDL, however such particles lack receptor competency. Apo B may be grafted onto such microemulsion particles, however, the grafting process still requires a source of the protein from fresh plasma.

Apo B is difficult to graft onto microemulsion particles partly because of its large size and a tendency for it to aggregate due to its amphipathic character. As such, grafting of Apo B onto microemulsion particles is not satisfactory because of inter alia inherent problems associated with the grafting-on process, and instability of the Apo B component.

It has now been found that a non-naturally occurring LDL can be produced which possesses LDL receptor competency, yet does not require the use of substantially whole Apo B or substantially whole analogues thereof. Furthermore, a process for the production of non-naturally occurring LDL has been developed which does not require the use of plasma derived LDL and/or plasma derived Apo B.

SUMMARY OF INVENTION

An object of the present invention is to provide a non-naturally occurring LDL possessing Apo B receptor competence.

Another object of the present invention is to provide a process for producing non-naturally occurring LDL particles.

These and other objects of the invention will become apparent from the following description and examples.

STATEMENT OF INVENTION

According to a first aspect of the present invention there is provided a non-naturally occurring, receptor competent LDL particle comprising at least one peptide component wherein the said peptide component comprises at least a binding site for an Apo B protein receptor and at least one lipophilic substituent.

A non-naturally occurring LDL particle is one which is not found occurring naturally in vivo. A non-naturally occurring LDL must be receptor competent i.e. capable of binding to Apo B receptors and/or capable of eliciting an Apo B protein-like physiological effect on and/or after binding. Thus, the non-naturally occurring LDL particle comprises at least a sequence of amino acids such as a protein, polypeptide or peptide capable of binding to Apo B receptors, which polypeptide may or may not be identical in respect of its binding region with the amino acid sequence of an Apo-B binding site, for example, an Apo B 100 binding site or physiologically functional peptide analogues thereof. Naturally, the skilled addressee will appreciate that the polypeptide capable of binding to Apo B receptors on target cells, such as cancer cells expressing Apo B receptors, is able to elicit an Apo B protein-like physiological effect on and/or after binding i.e. to be receptor competent.

The LDL particle comprises at least two components, a lipid component (L-component) and a peptide component (P-component). The L-component generally comprises a lipid emulsion comprising a core of lipophilic molecules such as cholesteryl esters, for example, cholesterol oleate, cholesterol linoleate, cholesterol stearate and the like. Other suitable lipophilic core molecules can comprise triglycerides, for example, triolein, plant oils such as soya bean oil and even lipophilic drugs, for example, estramustine, prednimustine and lipophilic modifications of known drugs, such as anti-cancer drugs, for example, cholesteryl esters of methotrexate and the like. The core of the L-component is typically solubilised by a lipid, such as an amphiphilic lipid comprising a charged or hydrophilic group. Such amphiphilic lipids include unesterified cholesterol and suitable non-ionic surfactants as well as phospholipids such as phosphatidyl choline, sphingomyelin and phosphatidyl glycerol. Preferably, the cholesteryl esters are solubilised by a monolayer of phospholipid. The preparation of the L-component is known in the art and may be performed using a variety of methods as described in the art, e.g. Ginsburg, G. S. et al (1982) J. Biol. Chem 257 (14) pp 8216–8227; Owens M. D. and Halbert G. W. (1993) J. Pharm. Pharmacol. 45 (Suppl.) p68P; Owens M. D. and Halbert G. W. (1995) Eur. J. Pharm. Biopharm 41 (2) pp 120–126, herein incorporated by reference.

Preferably, the L-component is made up of at least two biologically acceptable components. A first component can be a biologically acceptable saturated or unsaturated long chain charged polar component such as a phospholipid. Examples of suitable charged polar components include phosphatidyl choline (PC), phosphatidyl serine (PS), phosphatidyl glycerol (PG), sphingomyelin, and unesterified cholesterol and the like. The second component can be a biologically acceptable lipophilic component such as a cholesteryl ester, for example cholesteryl oleate. Biologically acceptable components are ones which may be administered to cells in vitro or in vivo and which have substantially no deleterious effect on cell viability. In a preferment the L-component can comprise three or more components in a defined ratio, such as a molar ratio, for example, phospholipid; triolein; cholesteryl ester (P:T:C) The molar ratio may be in any molar ratio as long as the components are capable of forming an L-component suitable for use in the preparation of non-naturally occurring LDL particles of the present invention. The molar ratio of outer core solubilising lipid such as phospholipid (PL) sphingomyelin (SM), phosphatidyl choline (PC) and unesterified cholesterol (UC) to core lipid such as cholesteryl ester (CE), triolein (TO) cholesteryl oleate (CO) or lipophilic drug can be in the range of from about 0.7:1 up to 5:1, preferably 1:1 to 3:1 depending on design. A preferred ratio of PL:CE is about 2:1. Where a third L-component is not employed the ratio of PL:CE can be in the range of from about 1:1 to about 2:1. A suitable molar ratio for a three component system such as a phosphatidylcholine: triolein: cholesteryl oleate is 3:2:1 respectively.

A suitable molar ratio for a five component system comprising three outer core lipids and two core lipids may lie in the range of from 0.7–6.5:0–2:0–1 (outer core lipid): 0–5:0–2.5 (core lipid). Preferably, the molar ratio lies in the range of from 2.5–4.5:1–2:0.5–1 (outer core lipid): 2–4.5:1–2.5 (core lipid). More preferably the molar ratio lies in the range of from 4–4.5:1.5–2:0.7–0.9 (outer core lipid): 4–4.5:1.8–2.2 (core lipid). Suitable outer core lipids may be selected from PC, SM, UC and PL. Suitable core lipids may be selected from TO, CE and CO. The man skilled in the art will appreciate that other suitable outer core lipids and core lipids may be used in the present invention. An example of a five component system is PC:SM:UC (outer core lipid): TO:CO (core lipid). The components of such a five component system may be present in molar ratios as indicated above.

Generally, the droplet diameter of lipid microemulsions employed in the non-naturally occurring lipoprotein particles of the invention should be capable of functioning as lipoprotein particles in vivo, ex vivo or in vitro. The diameter of the non-naturally occurring LDL particles can be up to about 50 nm, preferably from about 10 nm up to about 35 nm depending on the method of preparation and/or molar ratio such as a PL:CE molar ratio, employed.

Peptide components for use in forming LDL particles a: the invention contain at least one lipophilic substituent or moiety capable of acting as an "anchor" for anchoring the peptides to the L-component. Lipophilic moieties or substituents may be derived from biologically compatible lipophilic compounds such as cholesterol, retinoic acid, $C_{10}$–$C_{22}$ fatty acids such as stearic acid ($C_{18}$) and the like. The lipophilic moiety/substituent can be placed in contact with the amino and/or carboxy terminus of the peptide via chemical means such as covalent bonding or ionic bonding known in the art. The man skilled in the art will appreciate that peptides of the invention can be assembled using standard Fmoc protocols of the Merrifield solid phase synthesis method. The lipophilic substituent, such as retinoic acid can be activated and attached to the peptide N-terminus using a standard peptide coupling cycle. Initially an acid labile linker such as 3-methoxy-4-hydroxymethylphenoxyacetic acid is attached to the resin support and esterified with the first amino acid (C-terminus) of the target peptide. When peptide assembly is complete the ester to the linker can be hydrolysed, allowing removal of the fully protected peptide, for example with trifluoroacetic acid (TFA) eg. 1% TFA, in dichloromethane which can subsequently be evaporated off. At such a stage, the available functional group is the peptide carboxyl, which can be activated with for example one equivalent of dicyclohexylcarbodiimide (DCC) in dimethylformamide (DMF) and coupled to a lipophilic molecule, such as cholesterol (10 equiv), to yield ester. Evaporation of the solvent and treatment with TFA, e.g. 95% TFA, deprotects the amino acid side chains, completing the synthesis. The complete peptide can then be concentrated and precipitated with, for example, diethyl ether to give a solid which can then be washed as necessary to remove any remaining protecting group fragments and excess cholesterol.

N-terminal modifications, such as retinoic acid and stearate addition, targeted at primary amines can be used in the synthesis of modified peptides of the invention using techniques known in the art. Preferably, peptides capable of being utilised in the invention are amphipathic in nature, i.e. possess lipophilic and hydrophilic groups. Suitable hydrophilic groups include hydroxyl, carboxylic and amino groups. Where the peptides are amphipathic in character, the hydrophobic group and hydrophilic groups may be located at any suitable point thereon via appropriate side chains. Preferably the hydrophobic groups and hydrophilic groups are located either at the amino terminus and carboxy terminus of the peptide respectively or vice versa.

In an aspect of the invention there is provided non-naturally occurring LDL particles comprising peptides wherein the amino acid sequence of the binding site of said peptides are selected from the group: amino acids having basic side chains, amino acids having aliphatic side chains, and amino acids having aliphatic hydroxyl side chains.

In this aspect of the invention, the peptides of the non-naturally occurring LDL of the invention may display substantial, little or no similarity and/or identity with the amino acid sequence of the Apo B binding region. Preferably, the peptides display substantial similarity and/or identity with the amino acid sequence of the Apo B binding region.

The amino acid sequence which makes up the peptide capable of being grafted onto the lipid component of the LDL of the present invention can be selected from the group of amino acids having basic side chains e.g. lysine, arginine and histidine; amino acids having aliphatic side chains e.g. glycine, alanine, valine, leucine and isoleucine; amino acids having aliphatic hydroxyl side chains e.g. serine and threonine, and derivatives thereof.

Where the binding region amino acid sequence is substantially dissimilar to the binding region sequence of Apo B with respect to the order of amino acids incorporated thereinto, the amino acids selected for inclusion into the binding region of the amino acid sequence can be selected from substantially the same amino acids as those making up the Apo B binding region sequence. Naturally, the skilled addressee will understand that conservative replacement and/or substitutions as herein described may also be made to such binding regions.

In a preferment there is provided a non-naturally occurring LDL particle comprising at least one amino acid sequence including an Apo B binding region capable or interacting with an Apo B receptor.

Naturally, the skilled addressee will appreciate that such amino acid sequences making up functional peptides or polypeptides suitable for use in the present invention must be receptor competent as defined herein. Thus, synthetic or semi-synthetic peptides and/or polypeptides and analogues thereof capable of binding to Apo B receptors are encompassed by the present invention.

In a preferment, the amino acid sequence can comprise either or both of the Apo B binding site sequence(s) depicted below in the same peptide or in the form of dimers or in different peptides:

(1) Lys Ala Glu Tyr Lys Lys Asn Lys His Arg His (SEQ ID NO: 1);

or (2) Thr Thr Arg Leu Thr Arg Lys Arg Gly Leu Lys (SEQ ID NO: 2);

and analogues thereof which are capable of binding to the Apo B100 receptor site.

The amino acid sequence can be of any length provided that it is capable of being grafted onto the lipid component under grafting conditions as described herein. The amino acid sequence may include sequences of up to about 500 amino acid residues long comprising sequences (1) and/or (2) above. Sequences (1) and (2) are known Apo B binding site sequences identified from the human Apo-100 protein as described by Knott T. J. et al Nature Vol. 323 October 1986 p 735. For example, an amino acid sequence could comprise the sequence from amino acid 3079 to about position 3380 of FIG. 1, p 735 (Knott et al supra). The amino acid sequence can comprise at least a single Apo B binding site sequence and can be from about 8–200 amino acid residues in length, or a shorter sequence of from about 8–50 amino acid residues in length, preferably from about 9 to 30 amino acid residues in length. Examples of suitable peptide sequences include those as depicted in FIG. 7 herein. Naturally, the skilled addressee will appreciate that practical considerations such as the ability of the amino acid sequence to bind to receptor and ability to synthesise the peptide sequence generally means that the shorter amino acid sequences are preferred. The skilled addressee will appreciate that natural variations in the amino acid sequences comprising amino acid substitutions, deletions and/or replacements are encompassed by the present invention. Furthermore, the skilled addressee will also appreciate that amino acid substitutions, deletions and/or replacements can be made to the amino acid sequence so long as such modifications do not substantially interfere with the ability of the amino acid sequence to bind to a binding site and thereby elicit a physiological response. For example, conservative replacements may be made between amino acids within the following groups:

(i) Lysine and arginine;
(ii) Alanine, serine and threonine;
(iii) Glutamine and asparagine;
(iv) Tyrosine, phenylalanine and tryptophan; and
(v) Leucine, isoleucine, valine and methionine.

so long as the physiological function of the peptide is not substantially impaired.

The invention further includes substantially isolated proteins having a substantially similar activity/function to the peptides of the instant invention and which have an amino acid sequence which comprises at least 70% similarity, that is, identity, to the sequence of peptide (1) and/or peptide (2) above when aligned optimally therewith. It is preferred that such a degree of similarity, that is identity, is at least 80%, more preferred that such a degree of similarity is 90% or higher. In the context of the present invention two amino acid sequences with at least 70% similarity to each other have at least 70% identical or conservatively replaced amino acid residues in a like position when aligned optimally using computer programs known in the art, such as BLAST and FASTA.

In a further aspect of the invention there is provided use of non-naturally occurring LDL particles as drug-targeting vectors. Such drug targeting vectors can be used in the treatment of cancerous cells and the like.

In another aspect of the invention there is provided a process of producing a non-naturally occurring, receptor competent LDL particle possessing Apo B receptor competency which comprises:

i) forming a lipid component from lipophilic molecules and amphiphilic lipid molecules; and ii) contacting at least one peptide with a lipid component formed in i) wherein the at least one peptide comprises at least a lipophilic substituent and at least a binding region capable of interaction with an apoprotein B receptor.

In a further aspect of the invention there is provided use of an nLDL particle as a drug targeting vector, in particular in the treatment of cancerous cells comprising Apo B protein receptors in a patient.

In a still further aspect of the invention there is provided use of an nLDL particle in the manufacture of a medicament for the treatment of disease, in particular cancer. Thus, there is provided use of an nLDL particle in the manufacture of a drug targeting vector comprising a medicament therein for the treatment of cancerous cells comprising Apo B protein receptors.

The skilled addressee will appreciate that non-naturally occurring, receptor competent LDL particles of the invention may be administered to a patient along with conventional vehicles or carriers typically used in drug and vesicle presentation such as water, physiologically acceptable saline solutions, buffers and the like.

As a further aspect of the invention there is provided a Pharmaceutical formulation comprising a non-naturally occurring receptor competent LDL together with a pharmaceutically acceptable carrier. Pharmaceutically acceptable carriers may be selected from conventional carriers commonly employed in the art.

Additionally, there is provided a method for the treatment of cancer in a patient which comprises administering to the patient a clinically useful amount of a non-naturally occurring LDL particle comprising an anti-cancer drug.

The lipid component is as hereinbefore described as are the types of peptides which may be employed.

The following Figures are provided to Illustrate the present invention, and should not be construed as limiting thereof.

FIG. 1: Proliferation of U937 Cells in RPMI supplemented with Different Lipid Sources.

Legend: Mean±standard deviation (n=3). Cells were seeded at $1\times10^5$ in 75 $cm^2$ flask containing 25 ml of RPMI supplemented with: □ Serum 10% v/v, ■ Delipidated Foetal Calf Serum 5% v/v, ▲ No additions, ◆ LDL, ● Control microemulsion. LDL and control microemulsion were added at an equivalent cholesterol concentration (0.08 mmol/l) to Foetal Calf Serum. At 24 hour intervals, 0.5 ml of cell suspension was removed and counted.

Figure 2:
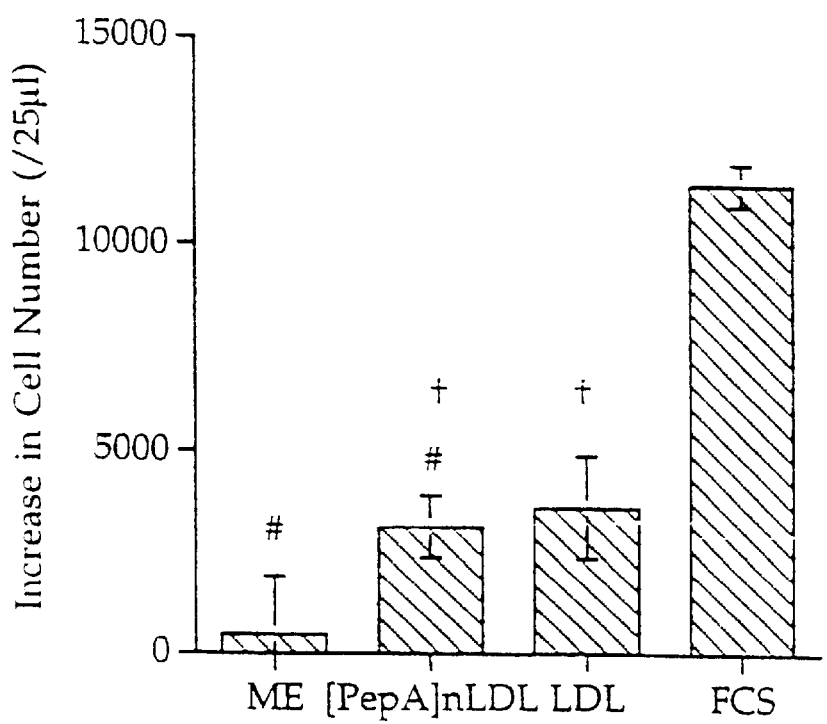

FIG. 2: Proliferation of U937 induced by Different Lipid Sources.

Legend: Mean±standard deviation (n=3). Result expressed as increase in cell number after 72 hours relative to mean result of control media with no additions. Microemulsion (ME) without peptide. Cholesterol concentration 0.08 mmol/l, Peptide concentration 0.03 mol/mol cholesterol oleate. No DFCS was used in any of the experiments. + No significant difference p>0.05. # Significant difference p<0.05

Figure 3:
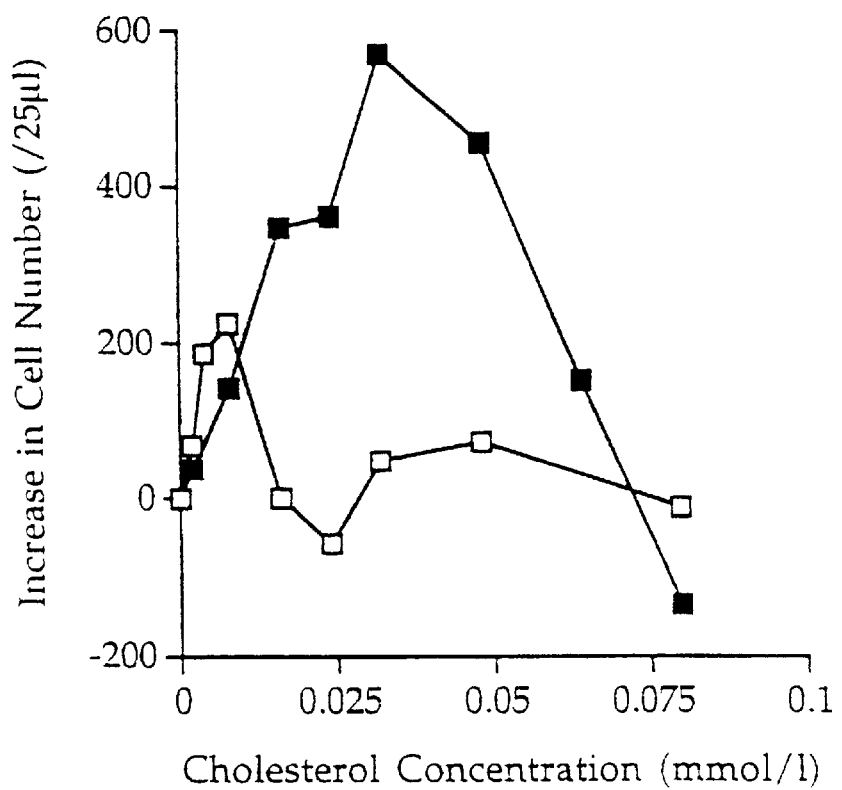

FIG. 3: Effect of Cholesterol Concentration and Delipidated Serum on the Growth of U937 Cells Supplemented with nLDL.

Legend: Mean (n=2). Result expressed as increase in cell number after 72 hours relative to mean result of control media with no additions. Open symbols {Peptide D} nLDL, without DFCS, filled symbols {Peptide D} nLDL supplemented with DFCS 5% v/v. Peptide concentration 0.03 mol/mol cholesterol oleate.

Figure 4A:
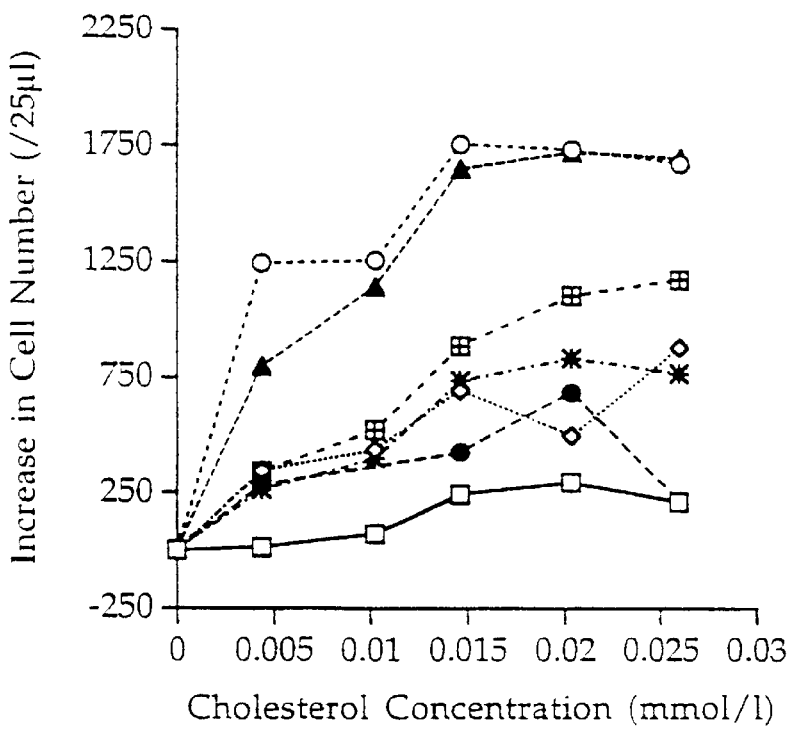

FIG. 4a: Growth of U937 Cells Induced by Different nLDL Preparations.

Legend: FIG. 4a. Mean±standard deviation (n=8). Result expressed as increase in cell number after 72 hours relative to mean result of control media with no additions. Peptide concentration 0.03 mol/mol cholesterol oleate. □ Microemulsion control; ◇ [Peptide A] nLDL; ○ [peptide B] nLDL; ▲ [Peptide C] nLDL; ▩[Peptide D] nLDL; * [Peptide E] nLDL; ● LDL. All supplemented with DFCS 5% v/v.

Figure 4B:
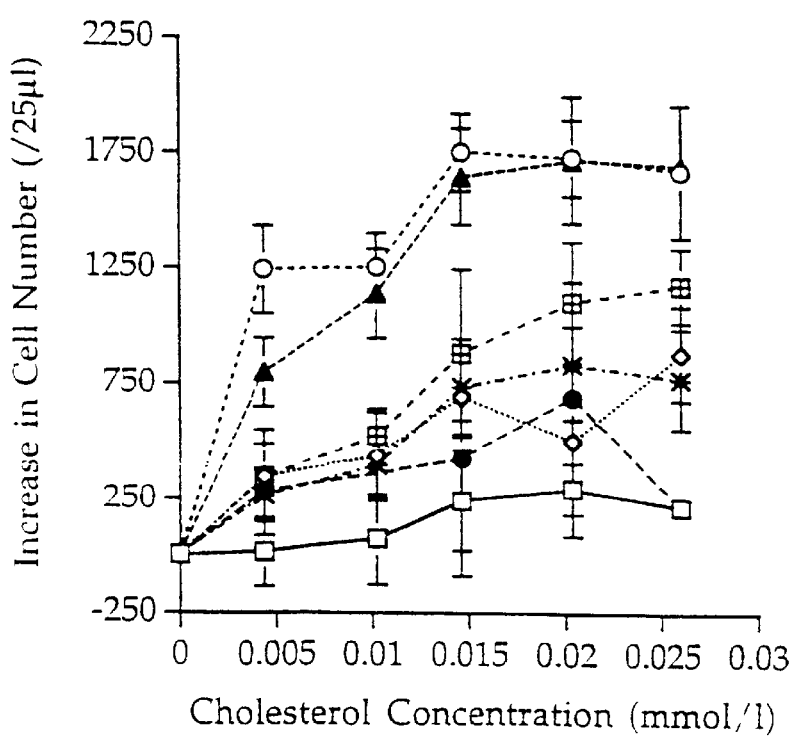

FIG. 4b: As for FIG. 4a, no standard deviations plotted.

Figure 5:
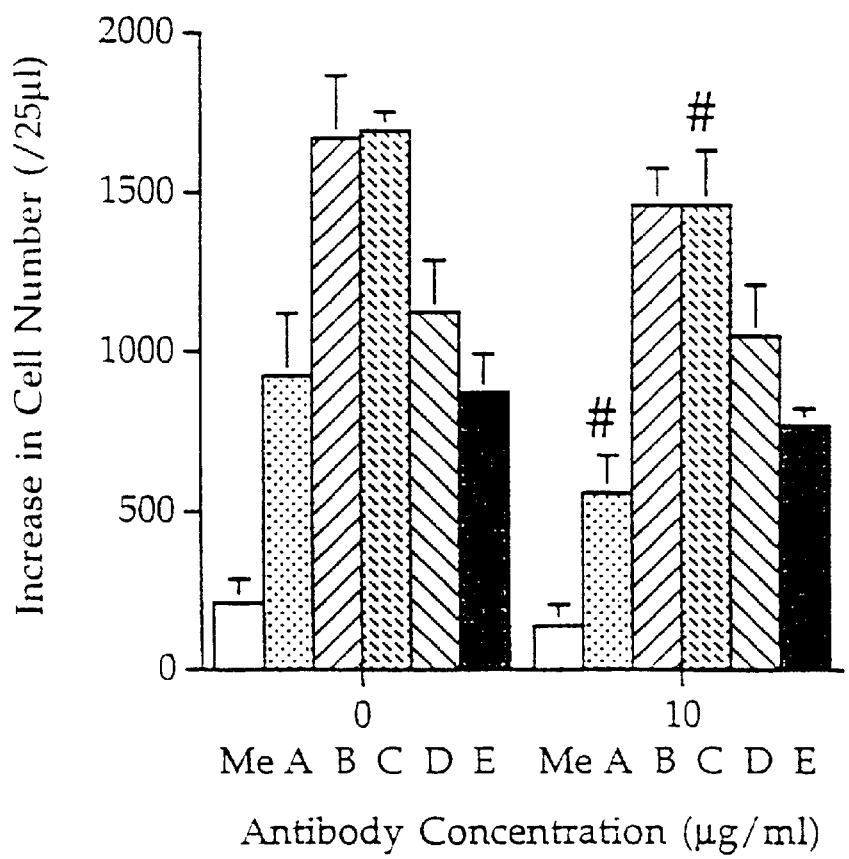

FIG. 5: Effect of Anti-LDL Receptor Antibody on the Growth of U937 Cells Induced by different nLDL preparations.

Legend: Mean±standard deviation (n=4). Result expressed as increase in cell number after 72 hours relative to mean result of control media with no additions. All supplemented with DFCS 5% v/v. Cholesterol concentration 0.026 mmol/l, peptide concentration 0.03 mol/mol cholesterol oleate. # Significantly less than antibody control (p<0.05).

Figure 6:
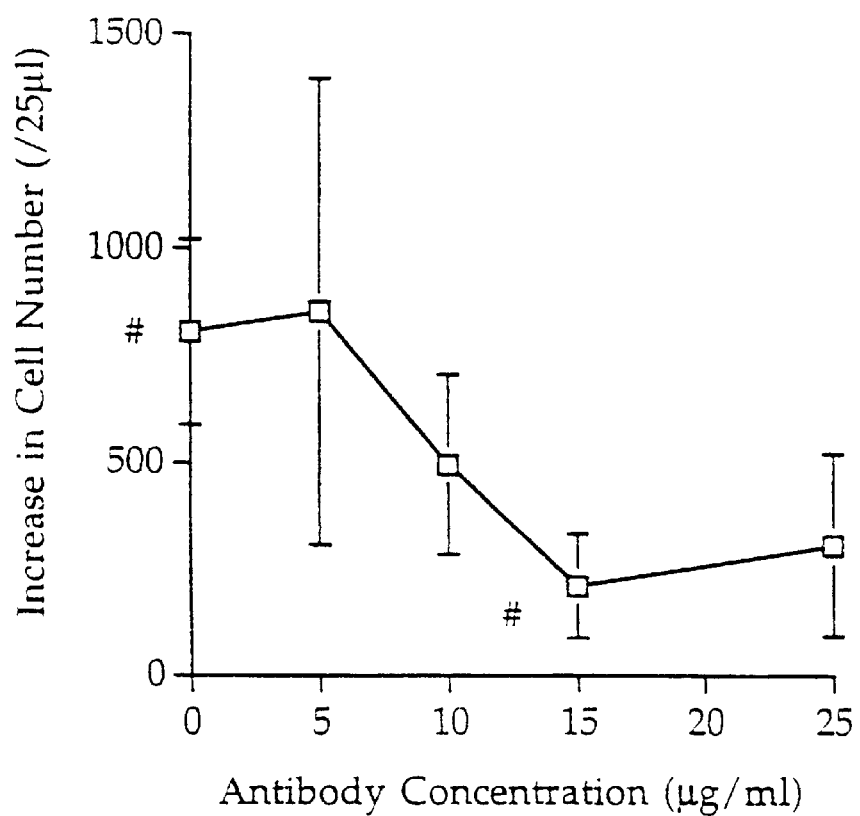

FIG. 6: Effect of increasing concentrations of Anti-LDL Receptor Antibody on the Growth of U937 Cells induced by {Peptide B} nLDL.

Legend: Mean±standard deviation (n=4). Result expressed as increase in cell number after 72 hours relative to mean result of control media with no additions. All supplemented with DFCS 5% v/v. Cholesterol concentration 0.033 mmol/l, peptide concentration 0.03 mol/mol cholesterol oleate. # Significant difference (p<0.05).

FIG. 7: Synthesised peptide analogues of the Apo-B 100 binding site (Peptides A–E inclusive).

Figure 8A:
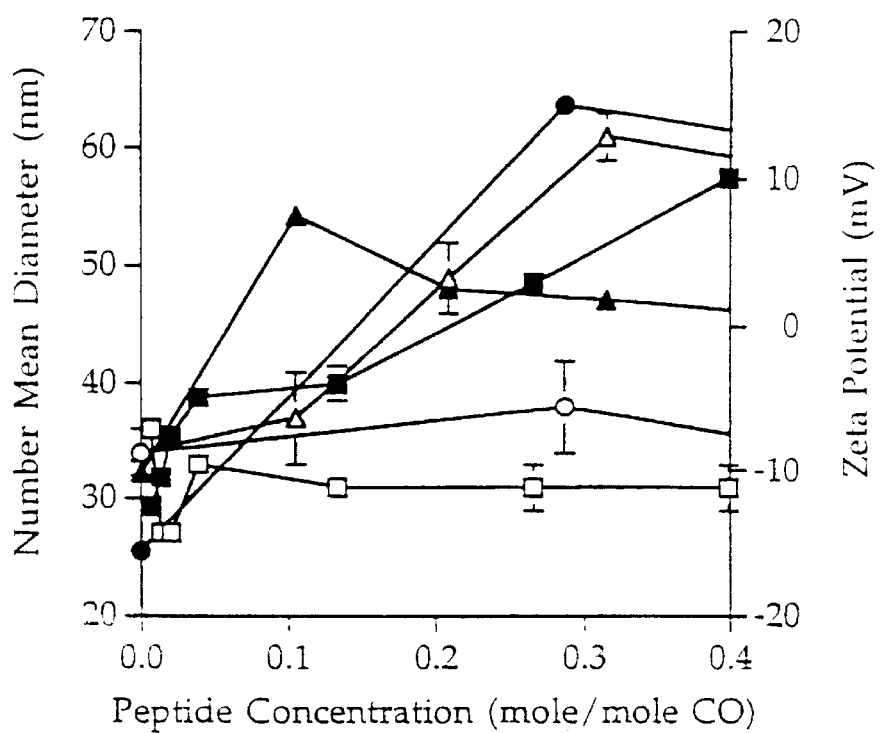
Figure 8B:
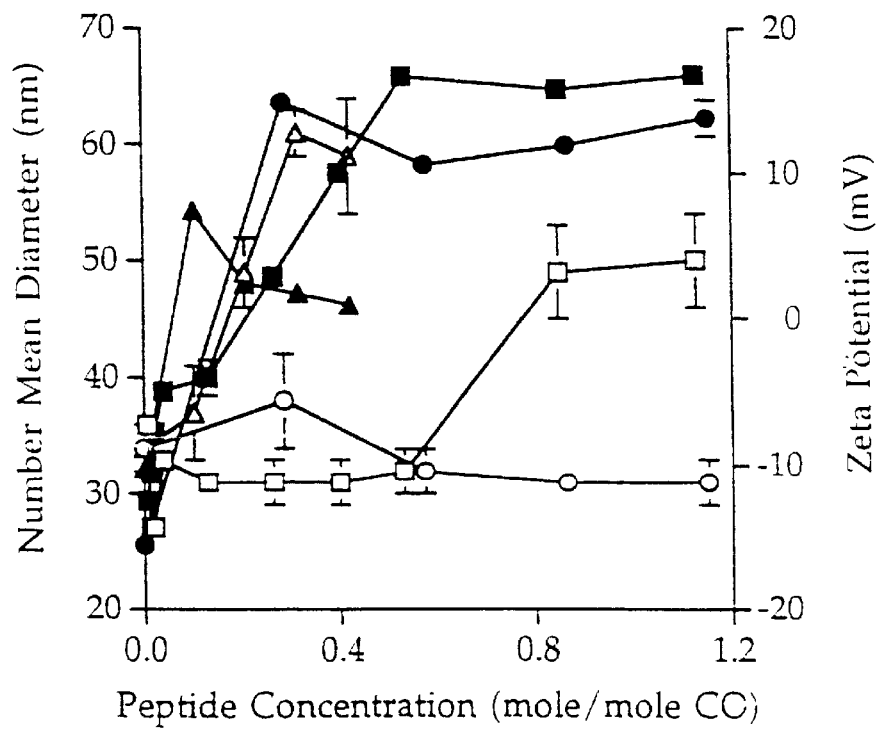

FIGS. 8(a) and 8(b): The effect of increasing peptide concentrations on the Number Mean Diameter and Zeta Potential of various nLDL preparations.

Legend: FIGS. 8(a) and 8(b). Open symbols Mean Number Diameter, closed symbols Zeta Potential. □ [Peptide A]-nLDL (PC:TO:CO, 3:2:1); ○ [Peptide B]-nLDL (PC:UC:TO:CO, 6.2:1:4.2:2.1); Δ [Peptide C]-nLDL (PC:UC:TO:CO, 6.2:1:4.2:2.1). Mean±standard deviation, n=10.

Figure 9A:
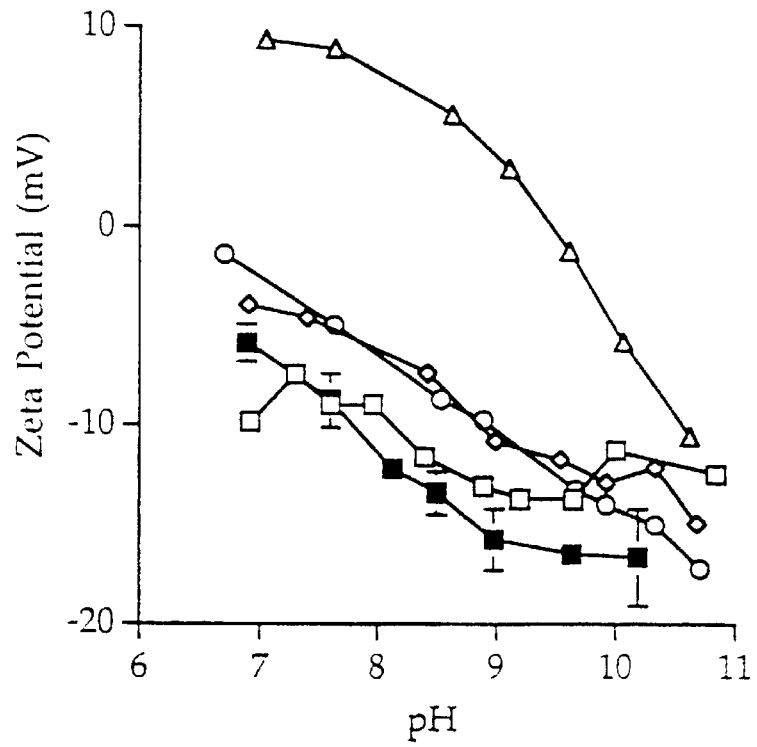

FIG. 9(a): The effect of pH on the measured Zeta Potential of various [Peptide A]-nLDL preparations.

Legend: FIG. 9(a). All preparations PC:TO:CO, 3:2:1. ■ DMSO treated control; □ 0.02 moles Peptide A/mole CO; ◇ 0.039 moles Peptide A/mole CO; ○ 0.106 moles Peptide/mole CO; Δ 0.532 moles Peptide A/mole CO. Mean±standard deviation, n=10.

Figure 9B:
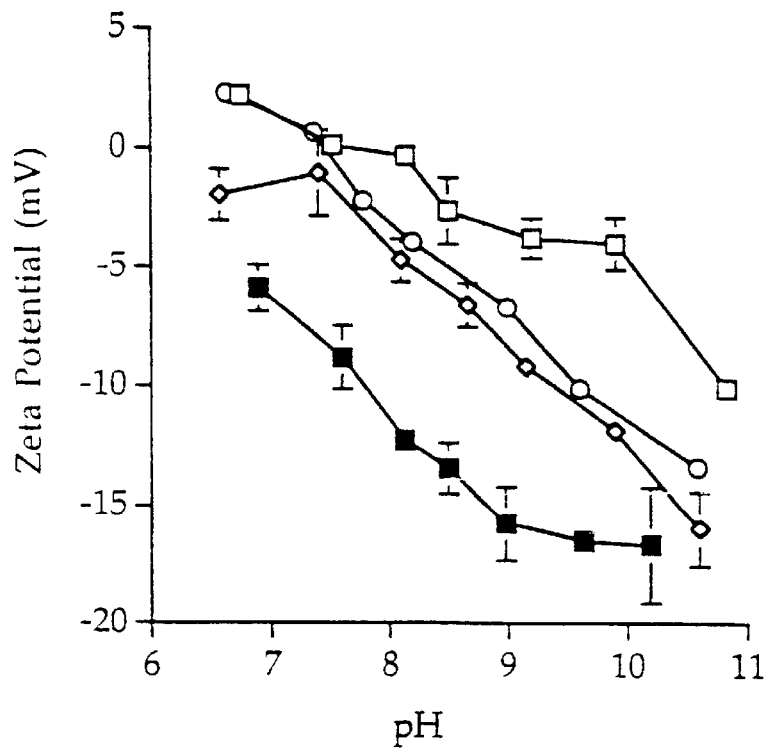

FIG. 9(b): The effect of pH on the measured Zeta Potential of various nLDL preparations.

Legend: FIG. 9(b). All preparations PC:TO:CO, 3:2:1. ■ DMSO treated control; □ [Peptide A]-nLDL 0.119 moles/mole CO; ◇ [Peptide B]-nLDL 0.112 moles/mole CO; ○ [Peptide C]-nLDL 0.111 moles/mole CO. Mean±standard deviation, n=10.

Figure 10A:
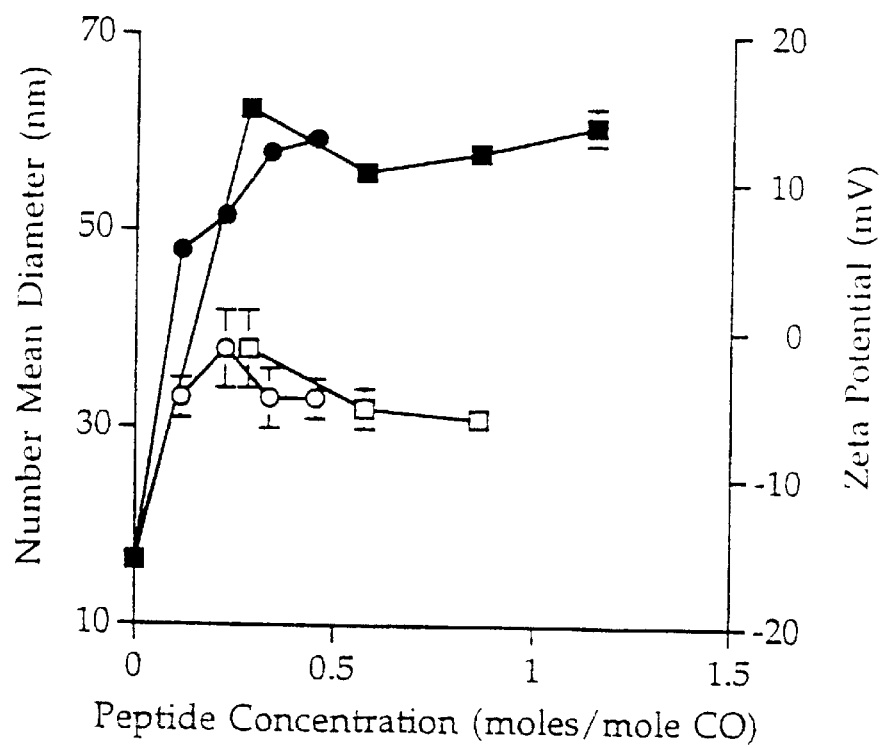

FIG. 10(a) The effect of microemulsion formulation on the measured Mean Number Diameter and Zeta potential of [Peptide A]-nLDL preparations.

Legend: FIG. 10(a). Open symbols Mean Number Diameter, closed symbols Zeta Potential. □ PC:TO:CO, 3:2:1, ○ PC:SM:TO:CO, 2.5:1:2.4:1.2; Δ PC:SM:UC:TO:CO, 4.4:1.8:1:4.2:2.1. Mean±standard deviation, n=10.

Figure 10B:
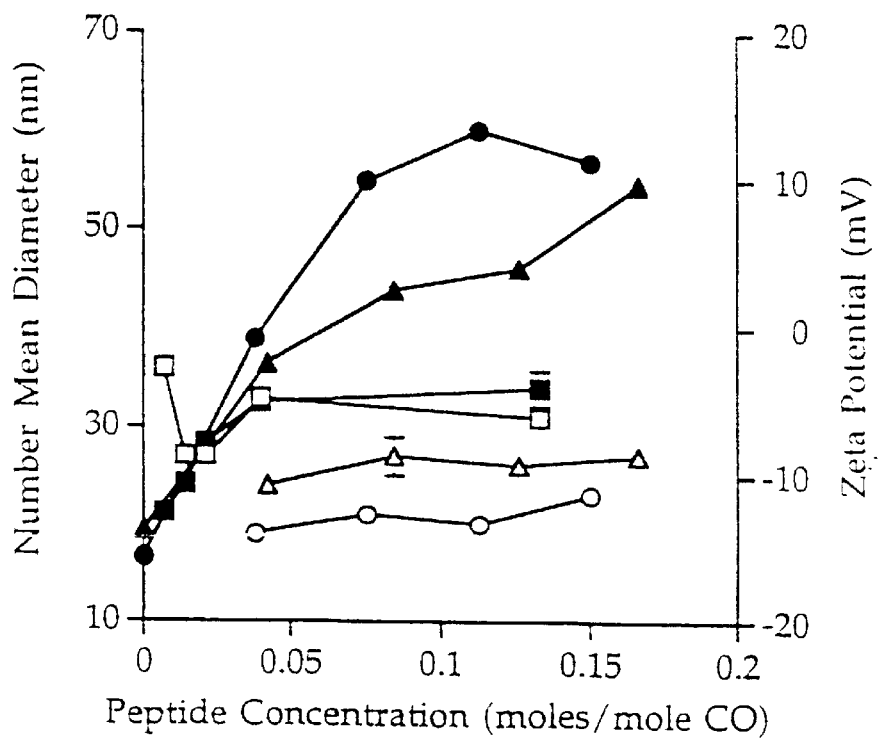

FIG. 10(b): The effect of microemulsion of formulation on the measured Mean Number Diameter and Zeta Potential of [Peptide B]-nLDL preparations.

Legend: FIG. 10(b). Open symbols Mean Number Diameter, closed symbols Zeta Potential. □ PC:UC:TO:CO, 6.2:1:4.2:2.1; ○ PC:SM:UC:TO:CO, 4.4:1.8:1:4.2:2.1. Mean±standard deviation, n=10.

FIG. 10(c): The effect of microemulsion formulation on the measured Mean Number Diameter and Zeta Potential of [Peptide C]-nLDL preparations.

Legend: FIG. 10(c). Open symbols Mean Number Diameter, closed symbols Zeta Potential. □ PC:UC:TO:CO, 6.2:1:4.2:2.1; ○ PC:SM:UC:TO:CO, 4.4:1.8:1:4.2:2.1. Mean±standard deviation, n=10.

FIG. 11: Total binding curves for various 14C-nLDL preparations to B16 cells in vitro at 4° C.

Legend: FIG. 11. Cells were serum starved overnight and cooled to 4° C. before the addition of media (also cooled to 4° C.) supplemented with DFCS and containing nLDL preparations at a cholesterol concentration of 0.08 mmol/l. All peptide concentrations were 0.03 mol/mol cholesterol. □ [NP]-nLDL; ◇ [Peptide A]-nLDL; ○ [Peptide B]-nLDL; Δ [Peptide C]-nLDL; ▩[Peptide D]-nLDL; + [Peptide E]-nLDL.

Figure 12A:
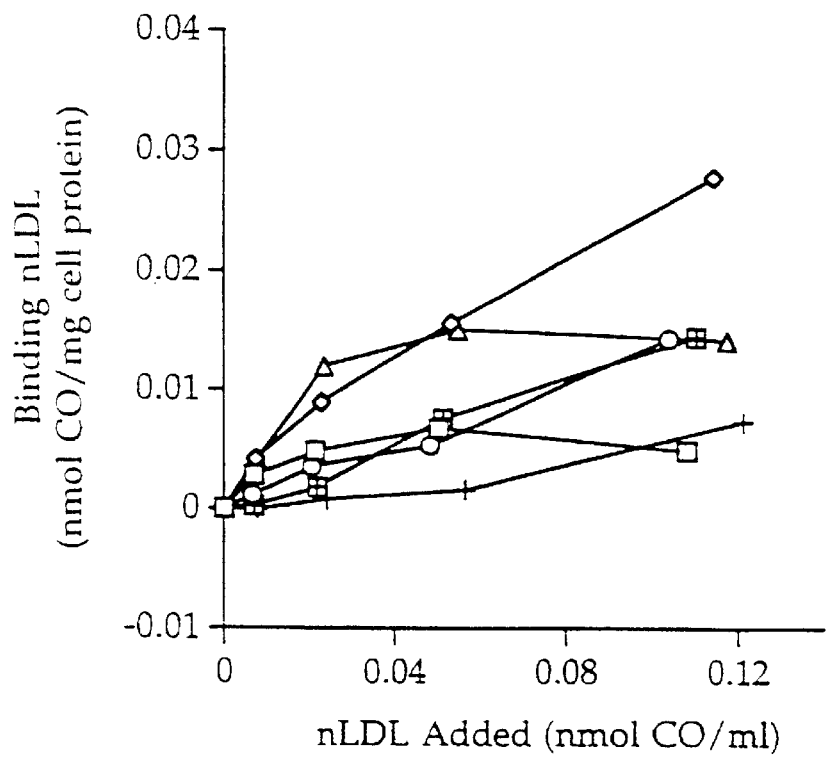
Figure 12B:
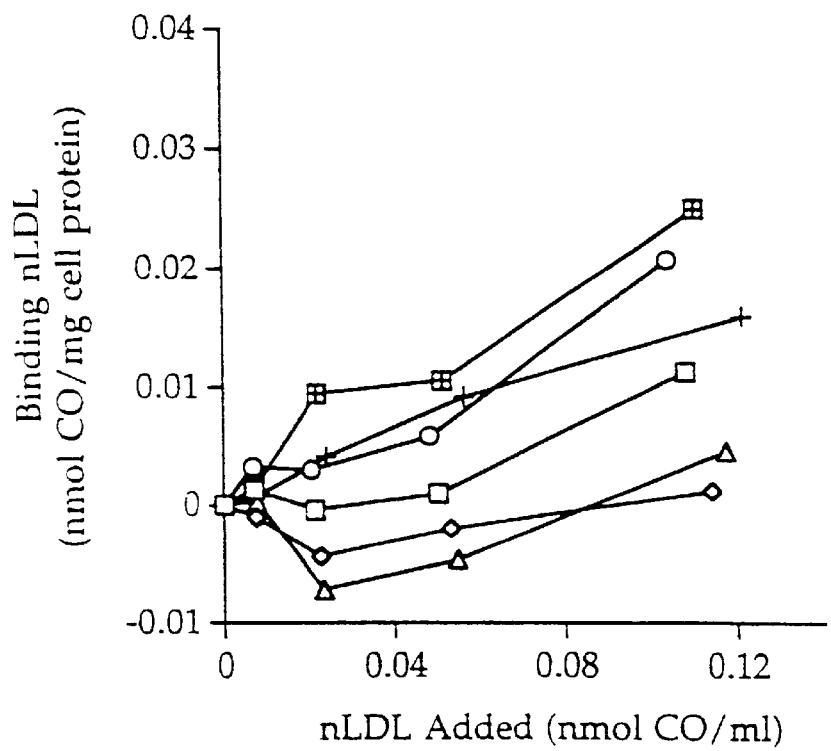

FIGS. 12(a) and 12(b): Non-specific (FIG. 12a) and specific (FIG. 12b) binding curves for various 12C-nLDL preparations to B16 cells in vitro at 4° C.

Legend: FIGS. 12 (a) and 12(b). Cells were serum starved overnight and cooled to 4° C. before the addition of media (also cooled to 4° C.) supplemented with DFCS and containing nLDL preparations at a cholesterol concentration of 0.08 mmol/l. All peptide concentrations were 0.03 mol/mol cholesterol. Values for non-specific binding obtained were measured using an excess of unlabelled nLDL, specific binding values calculated by subtracting non-specific binding from total binding. □ [NP]-nLDL; ◇ [Peptide A]-nLDL; ○ [Peptide B]-nLDL; Δ [Peptide C]-nLDL; ▩[Peptide D]-nLDL; + [Peptide E]-nLDL.

Figure 13:
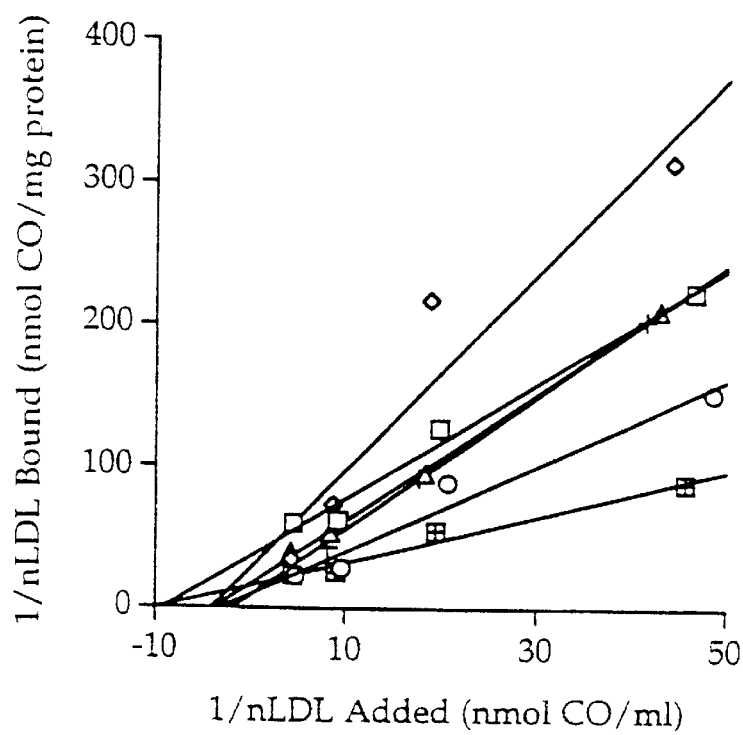

FIG. 13: Double reciprocal plots of total binding data for various 14C-nLDL preparations to B16 cells in vitro at 4° C.

Legend: FIG. 13. Experimental conditions as per FIGS. 12(a) and 12(b). Lines determined by linear regression, values calculated from data presented in Table 1. □ [NP]-nLDL; ◇ [Peptide A]-nLDL; ○ [Peptide B]-nLDL; Δ [Peptide C]-nLDL; ▩[Peptide D]-nLDL; + [Peptide E]-nLDL.

Figure 14:
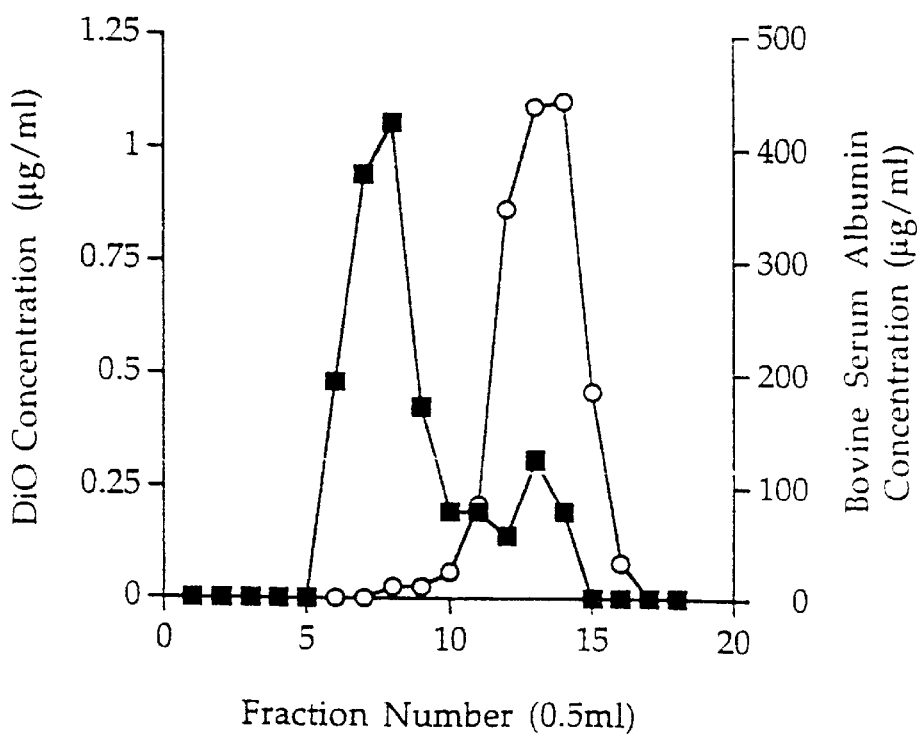

FIG. 14: Chromatography of DiO labelled nLDL after incubation with Bovine Serum Albumin.

Legend: FIG. 14. ■ DiO; ○ Bovine Serum Albumin. Sephacryl S-300 column (bed volume 9.1 ml). DiO labelled nLDL was mixed with PBS/BSA (2 mg/ml) and incubated at 37° C. before being added to column pre-equilibrated with PBS. Eluted fractions were analysed for DiO and protein content as described in methods. Values are single measurement of each fraction.

Figure 15:
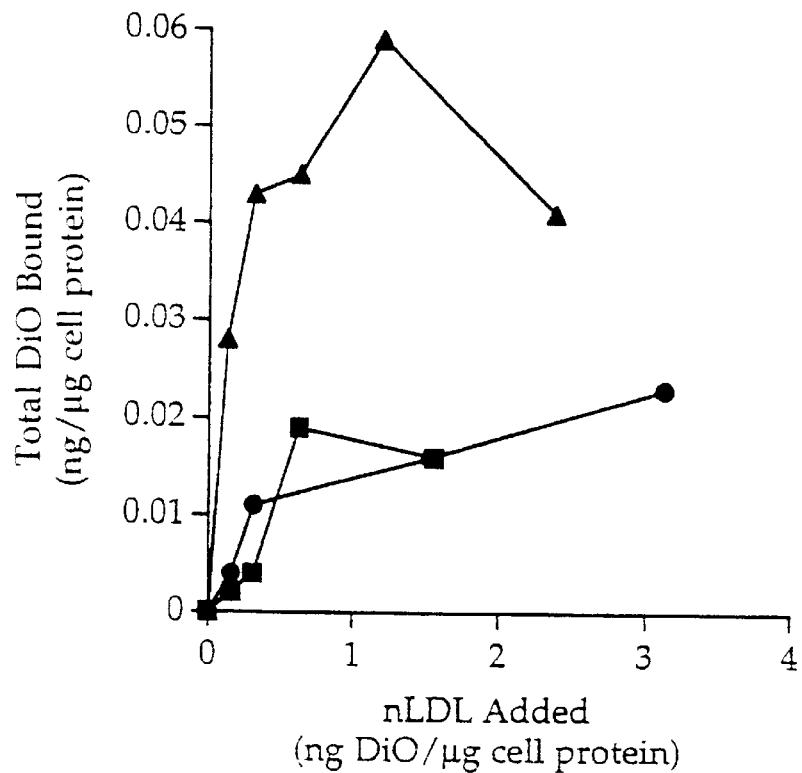

FIG. 15: Dose response of DiO labelled nLDL binding to B16 cells.

Legend: FIG. 15. Cells incubated at 4° C. for three hours, mean (n=5, observations varied by less than 16%), non-specific binding was not accounted for. ■ Microemulsion control; ● [Peptide A]-nLDL; ▲ [Peptide C]-nLDL.

Figure 16:
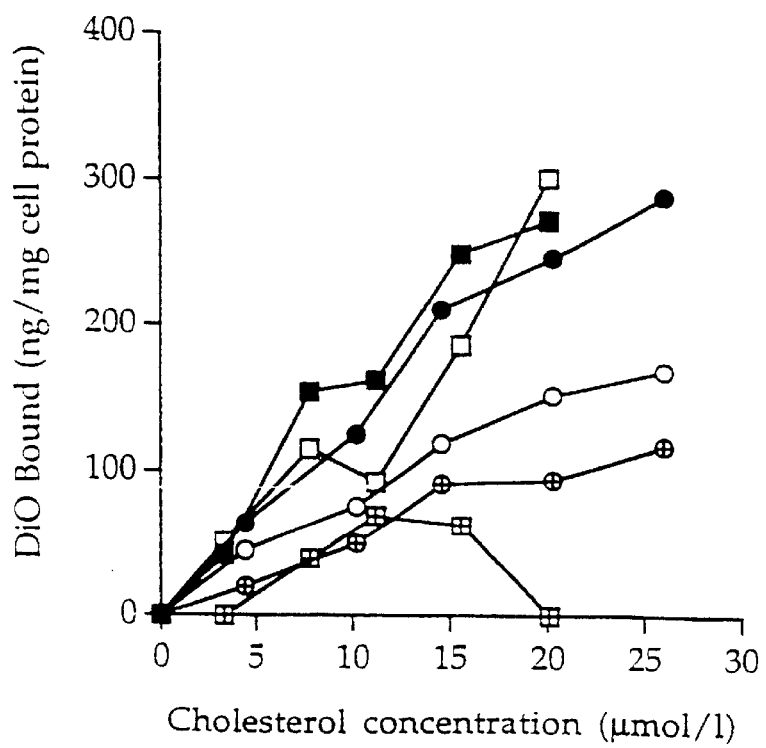

FIG. 16: Binding Characteristics of DiO labelled microemulsion and nLDL to B16 cells at 4° C.

Legend: FIG. 16. Cells incubated at 4° C. three hours, mean (n=5, observations varied by less than 16%). Specific High Affinity Binding was determined by subtracting non-specific binding (determined using a 100 fold excess of unlabelled ligand) from total binding. ■ Microemulsion total binding; □ microemulsion non-specific binding; ▩microemulsion specific binding; ● [Peptide A]nLDL total binding; ○ [Peptide A]nLDL non-specific binding; ⊕ [Peptide A]nLDL specific binding.

Figure 17:
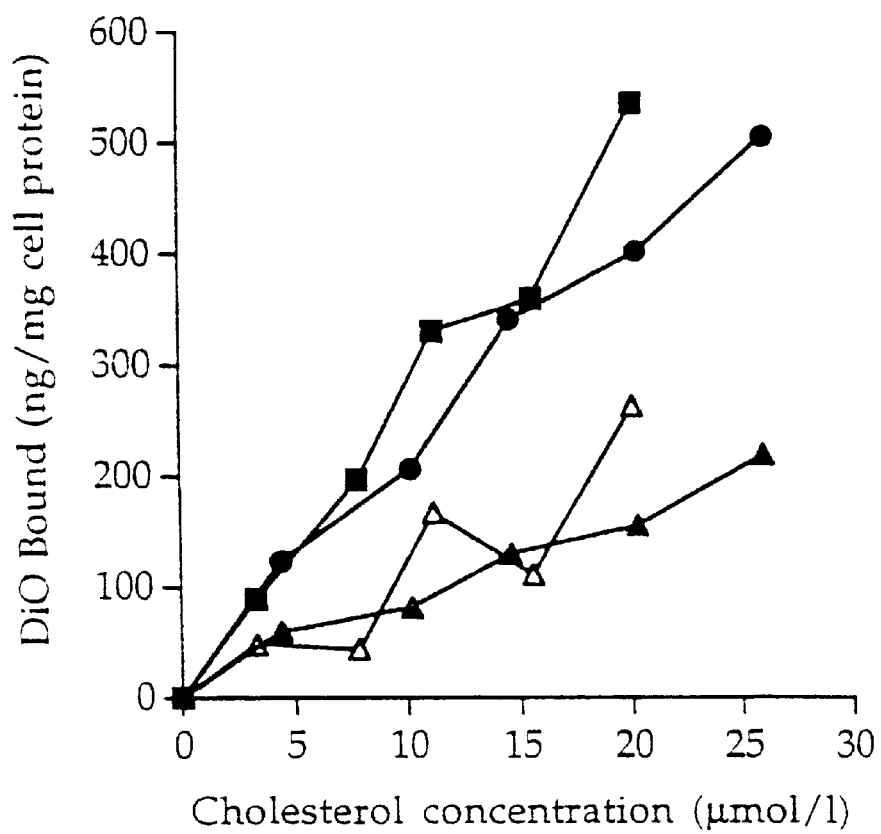

FIG. 17: Binding and Internalisation of DiO labelled microemulsion and nLDL to B16 cells at 37° C.

Legend: FIG. 17. Cells incubated at 37° C. for three hours, mean (n=5, observations varied by less than 16%). Specific High Affinity Binding was determined by subtracting non-specific binding (determined using a 100 fold excess of unlabelled ligand) from total binding. ■ Microemulsion total binding; Δ microemulsion internalisation, ● [Peptide A]nLDL total binding; ▲ [Peptide A]nLDL internalisation.

Figure 18A:
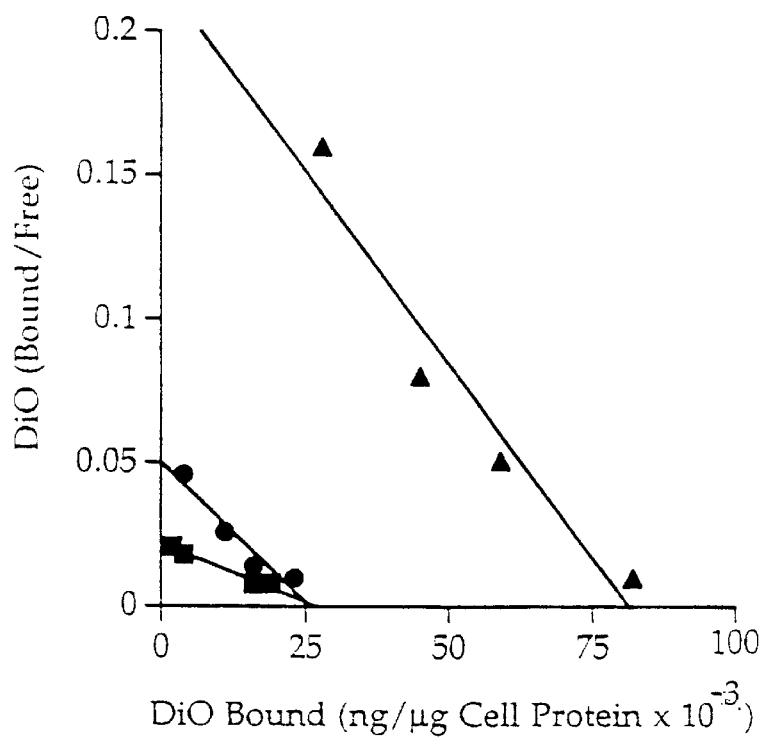
Figure 18B:
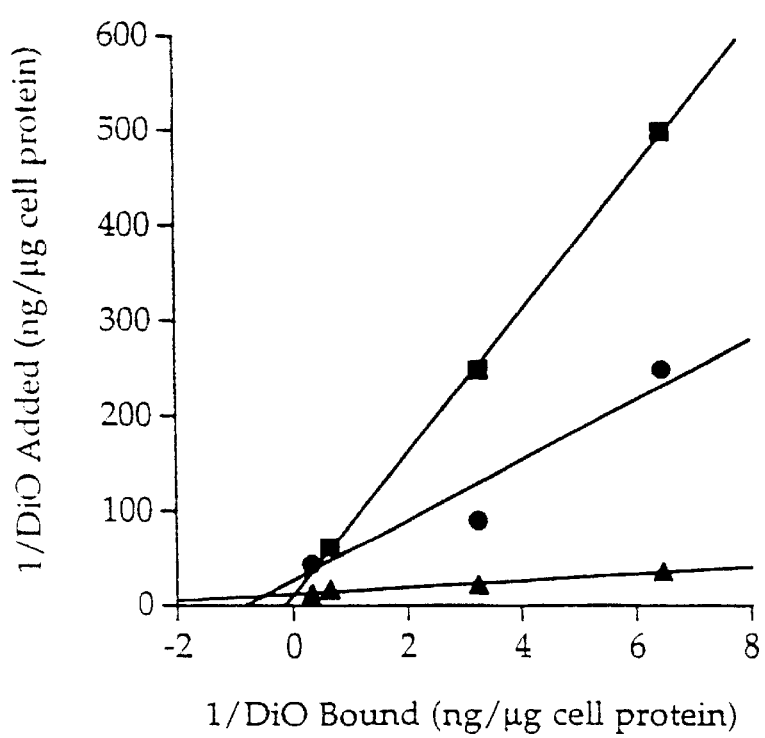

FIGS. 18(a) and 18(b): Scatchard and Double Reciprocal Plots of DiO labelled microemulsion and nLDL binding to B16 cells at 4° C.

Legend: FIG. 18(a). Scatchard Analysis of total binding at 4° C. after three hours, mean (n=5). ■ Microemulsion; ● [Peptide A]nLDL; ▲ [Peptide C]nLDL.

Legend: FIG. 18(b). Double Reciprocal Analysis of total binding at 4° C. after three hours, mean (n=5). Symbols as FIG. 18(a).

Figure 19:
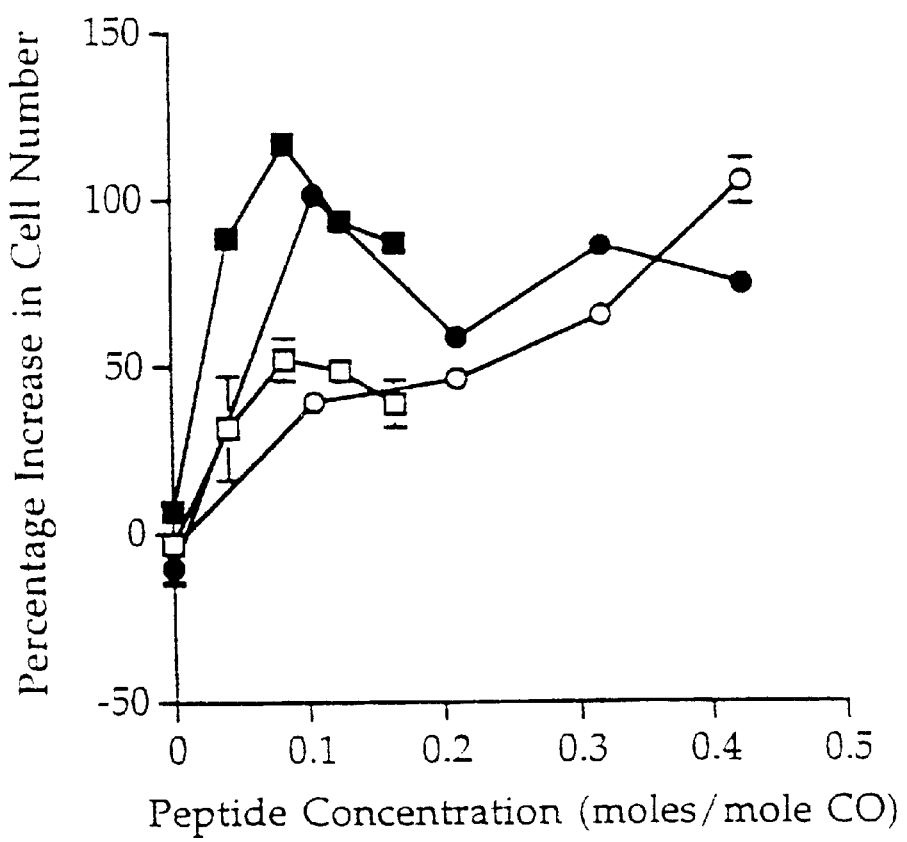

FIG. 19: The effect of ethinyl estradiol on [Peptide]nLDL U937 cell proliferation.

Legend: FIG. 19. Mean±standard deviation n=4. Results expressed as increase in cell number after 72 hours relative to mean result of control media with no additions. Open symbols no ethinyl estradiol, closed symbols ethinyl estradiol (2 μg/ml). □ [Peptide A]nLDL; ○ [Peptide B]nLDL. Cholesterol concentration 0.08 mmole/l.

The invention will now be illustrated with the following non-limiting examples.

EXAMPLE 1

Materials and Methods

Materials

Egg yolk phosphatidylcholine (PC) was purchased from Lipid Products, Surrey, United Kingdom and used without further purification (>99% pure). Tris(hydroxymethyl)-methylamine (Tris), hydrochloric acid (HCl), dimethylsulfoxide (DMSO) and t-butanol (all Analar grade) were obtained from Merck Ltd, Glasgow, United Kingdom. Triolein (99% pure, TO), cholesteryl oleate (98% pure, CO), phosphate buffered saline (PBS) tablets and the reagents used for cholesterol testing were purchased from the Sigma Chemical Company, Dorset, United Kingdom. The polycarbonate filters used in the extrusion process were obtained from Costar Corporation, Buckinghamshire, United Kingdom. Sterile, disposable 0.2 μm polysulfone filters used for filter sterilisation were purchased from Whatman Ltd. Maidstone, United Kingdom. Sterile, distilled water complying with the European Pharmacopoeia's water for injection monograph was purchased from Steripak Ltd, Runcorn, United Kingdom. All synthetic polypeptides were synthesised at Thistle Peptide Services (formerly BioMac) at the Department of Biochemistry, University of Glasgow. Peptide structures are listed in FIG. 7, material was supplied at greater than 90% purity and was used as received. All tissue culture materials (media, serum, culture flasks, pipettes and multi-well plates) Were obtained from Life Technologies Ltd., Paisley, United Kingdom. U937 cells were obtained from the European Collection of Animal Cell Cultures, Salisbury, United Kingdom. DFCS was prepared from FCS by the method of Rothblat et al [6]. Monoclonal anti-LDL receptor antibody (clone C7, code number RPN.537) was purchased from Amersham International and reconstituted with sterile water just prior to use.

Methods

Preparation of nLDL Particles

A 3:2:1 molar mixture of Phosphatidylcholine: Triolein: Cholesteryl Oleate (PC:TO:CO) was dissolved in chloroform/methanol 2:1 (V/V) and the solvent removed under a stream of nitrogen. The lipids were then re-dissolved and lyophilised from t-butanol for 24 hours (EF4 Modulyo Freeze Dryer, Edwards High Vacuum, Crawley, United Kingdom), then re-suspended in 0.01M Tris-HCl buffer (pH 8.0) to give a final concentration of 7 to 8 % w/v for extrusion. The lipid dispersions were sonicated under a stream of $N_2$ for two hours using a 250W sonicator, centrifuged at 10,000 rpm for 60 minutes (MSE Superspeed 75 Ultracentrifuge, MSE Ltd, London, United Kingdom) and then transferred to the Extruder vessel (Lipex Biomembranes Inc, Vancouver, Canada) which was maintained at 50–55° C. throughout. The lipid mixture was successively extruded through polycarbonate filters of pore size 0.1 and 0.05 μm using two stacked filters and at least four extrusions under 60 psig pressure provided by a nitrogen source[8]. Samples of lipid microemulsion were diluted with Tris-HCl buffer to give a cholesterol concentration of approximately 1 mmol/l and heated to 55° C. in a stirring water bath. Aliquots of peptide dissolved in DMSO were added under the surface of the stirring microemulsion, control experiments were performed with DMSO alone. The volume of DMSO added in each case was kept below 20 μl/ml of microemulsion mixture. The peptide-microemulsion complex was incubated at 55° C. for 15 minutes then dialysed overnight against 5 liter PBS. The resulting non-naturally occurring LDL (nLDL) were filter sterilised (0.2 μm) and stored at 4° C. under $N_2$ before use.

Analysis for Cholesterol Content

Microemulsions were assayed for cholesteryl ester content using the method of Allain et al[9]. The Cholesterol Reagent (cholesterol oxidase, cholesterol esterase, horseradish peroxidase, 4-aminoantipyrene, p-hydroxybenzenesulfonate and buffer) was warmed to 30° C. in a water bath. To 1.0 ml of reagent was added 0.01 ml of sample, blank (distilled water) or standard (Cholesterol Calibrator, 200 mg/100 ml). Reagent-sample mixtures were allowed to incubate at 30° C. for 10 minutes. The absorbance of each sample was measured at 500 nm on a spectrophotometer (Cecil CE272 Ultraviolet Spectrophotometer). All readings were complete within 30 minutes after the end of the incubation period. Cholesteryl oleate content was calculated by reference to the cholesterol standard.

Cell Culture

U937 stock cultures were grown at 37° C. in RPMI 1640 media supplemented glutamine (10 mM), gentamicin (50 μg/ml), fungizone (0.5 μg/ml) and 10% (v/v) foetal calf serum (FCS). Cells were maintained in a humidified 5% CO, atmosphere between $1-8\times10^5$ cells/ml and sub-cultured twice weekly.

Growth Assay

All growth assays were conducted over 72 hours in 24 well plates unless otherwise indicated. One day before each growth experiment, cells were centrifuged at 1500 rpm for 5 minutes and resuspended in RPM: medium containing 5% (v/v) delipidated foetal calf serum (DFCS) to initiate cholesterol starvation and up regulate LDL receptors. Cells were collected by centrifugation and seeded at 1×10⁵/well. Appropriate amounts of cholesterol (either LDL, microemulsion or nLDL) were then added after filtration (0.2 μm) and the well volume made up to 1 ml with RPMI containing 5% (v/v) DFCS. After 72 hours an aliquot of each well was diluted with PBS and the number of cells present determined in triplicate by Coulter Counter. Different concentrations were repeated four or eight times depending on the experiment. Three wells per experiment were checked at random before commencement of incubation to ensure a uniform cell density was achieved. This has previously been shown to be a contributing factor in the reproducibility of assay results [7]. In all cases, the mean starting cell densities of control resells were between 0.95 and 1.05×10⁵ cells/ml.

Results and Discussion

The results presented in FIG. 1 demonstrate that the growth of U937 was supported by FCS containing media and to a lesser extent by LDL but not by delipidated FCS or a microemulsion with a similar lipid composition to LDL. This result is consistent with published studies which prove U937 has no ability to synthesise cholesterol and overcomes this by receptor mediated uptake of LDL[3].

To determine whether non-naturally occurring LDL (nLDL) could also support cell growth, U937 cells were incubated with {A}nLDL at a cholesterol concentration equivalent to the optimum LDL concentration which produces maximal cell growth (0.08 mmol/l). The results presented in FIG. 2 demonstrate that {A}nLDL supported the proliferation of U937 cells in vitro. The growth increase was significantly greater ($p<0.05$) than that produced by microemulsion alone but not statistically different ($p>0.05$) from that supported by LDL. This strongly suggests nLDL uptake by U937 in a manner similar to LDL and which permits cellular proliferation. This result is due to the presence of the receptor peptide on the particle since control microemulsions do not exhibit this property.

The proliferation of U937 induced by LDL is dose dependent and saturable [3], experiments were therefore conducted to investigate if this was also true for nLDL. In FIG. 3 the effects of both increasing nLDL cholesterol concentration and adding DFCS to the media is presented. It can be clearly seen that there is an optimal cholesterol concentration and that DFCS enhanced the proliferation of [Peptide D]nLDL by U937 cells. The maximum DFCS induced increase in cell number was three times that of media containing no serum. The optimum cholesterol concentration of [Peptide D]nLDL in media containing DFCS (0.032 mmol/l) is comparable to that of U937 cells grown with LDL 0.0:26 mmol/l) [5]. However, in agreement with earlier findings using LDL, large concentrations of nLDL produced a reduction in cell number when compared with an untreated control. Optimum nLDL cholesterol concentrations (those which resulted in greatest proliferation) were also increased four fold by DFCS (from 0.008 mmol/l to 0.0:32 mmol/l) suggesting that serum promoted more efficient nLDL uptake.

In order to determine the effect of peptide configuration on U937 nLDL uptake, proliferation assays were conducted using five nLDL systems, see FIG. 7 for details of each peptide. All the nLDL systems over the range of cholesterol concentrations tested produced a significant proliferation ($p<0.05$ of U937 cells) (FIG. 4) when compared with microemulsion alone. The small proliferation supported by microemulsion without polypeptide at high concentrations may be due to weak non-specific phagocytic activity [10]. However the increases in cell number supported by five different nLDL systems (peptides A–E) strongly suggests that inclusion of the receptor peptide on the particle enhances uptake. Peptide B, C and D systems exhibit the greatest increase in proliferation and these contain either no C-terminal lipid anchor (peptide B and D) or the binding region of Apo B embedded in a 22 amino acid residue chain. The variation between systems indicates that peptide sequence and the presence of a C-terminal lipophilic anchor control the extent of proliferation. The least effective systems, peptides A and E contain either the shortest chain length with both C and N terminal lipid anchors (Peptide A.) or a non Apo B binding region sequence of amino acids (Peptide E).

LDL supported similar increases to nLDL Preparations containing peptides A, D and E but was three times less than [Peptide B] and [Peptide C]nLDL (FIG. 4). This may be due to the viability of commercially obtained LDL. The measured increases were ten times less than those reported by Frostegard et al [3] at a cholesterol concentration of 0.03 mmol/l or by Schewe et al,[4] using 20 μg/ml LDL cholesterol and by Sells and Barakat[5] including 10 μg/ml in the culture medium. This result illustrates the problem associated with the current requirements to isolate fresh LDL for in vitro or in vivo experiments.

To further determine that nLDL induced proliferation of U937 cells is due to receptor mediated uptake, cells were incubated with various nLDL preparations (cholesterol concentration 0.026 mmol/l) and a commercially obtained human anti-LDL receptor antibody. An antibody concentration of 10 μg/ml was chosen as this had previously been shown to reduce LDL (0.150 mmol/l) supported U937 growth to almost zero [3]. Incubation with the antibody produced a small decrease in the growth of U937 cells grown in media containing each of the nLDL preparations and Microemulsion (FIG. 5). The decreases for [Peptide A]nLDL [Peptide C]nLDL were statistically significant, however, cell numbers were not reduced to the level of control microemulsion.

In order to further investigate the effect of anti-LDL receptor antibody on U937 nLDL uptake, a range of antibody concentrations were tested for 72 hours in media containing [Peptide B]nLDL (0.033 mmol/l). [Peptide B]nLDL is the most effective nLDL in promoting U937 growth suggesting a maximal receptor interaction (see FIG. 4). Low antibody concentrations (5 μg/ml) had no effect on proliferation (FIG. 6), however higher concentrations produced a dose dependent, saturable inhibition. Even at antibody saturation (15 μg/ml) cell proliferation is significantly more ($p<0.05$) than control wells without lipid. The large inhibition of cell growth (74%, $p<0.05$) observed in this study at antibody saturation (15 μg/ml) further reinforces the supposition that nLDL induced cellular proliferation is via uptake by the LDL receptor.

The nLDL particles presented in this study exhibit a concentration dependent and saturable ability to induce cellular proliferation of U937 cells in vitro. This effect is stimulated by the presence of DFCS in the media and is inhibited by an anti-LDL receptor antibody. These results illustrate that nLDL mimics the effects of native LDL in the U937 cell proliferation assay and demonstrate that nLDL exhibits receptor competency. A comparison of nLDL systems also demonstrates that control of reception interaction is possible by alteration of the peptide sequence and by varying the number and location of the lipid anchors.

EXAMPLE 2

Materials and Methods

Materials, appropriate preparations of nLDL particles, and analysis of cholesterol content follow the outlines as for Example 1, above.

Photon Correlation Spectroscopy

Particle size analysis was carried out using photon correlation spectroscopy (Zetasizer® Model 4, Malvern Instruments, Malvern, (UK). Before analysis samples were diluted with Tris-HCl buffer (0.01M) and filtered (0.2 $\mu$m). Sizing measurements were carried out at a fixed angle of 90° to the incident beam. The correlator was operated in parallel mode to allow for more accurate size distribution measurements. The cumulants method of analysis was used to calculate the mean sample size weighted according to the intensity of scattered light (z-average diameter). Since this diameter is weighted strongly on favour of large particles, Rayleigh theory was used to convert intensity distributions into number distributions [12]. The viscosity and refractive index values of pure water were used in the size calculations. All results quoted are the mean and standard deviation of at least 10 measurements.

Zeta Potential Measurement

Samples were diluted 1 in 5 with 0.01M Tris buffer (pH 8.0) and zeta potential measured at 25° C. using the Zetasizer® 4 (Malvern Instruments). The applied voltage was 150V in each case and duty cycling was used to limit the cell current to 20 mA. All results quoted are the mean and standard deviation of at least 10 measurements.

Results and Discussion

The effects of increasing concentrations of the peptides on both diameter and zeta potential are presented in FIG. 8. All the peptides act to change measured zeta potential from a negative to a positive value but produce markedly different effects on particle diameter. Below 0.5 moles/mole Co Peptide A has no effect on size but produces an almost linear increase in zeta potential with concentration. Higher concentrations produce size increases but zeta potential plateaus at around +17 mV. Peptide B at low concentrations provides a dramatic reversal in zeta potential from around −15 mV to +15 mV without any change in size. Further concentration increases do not increase zeta potential which remains constant at +15 mV but size also remains constant. Peptide C around 0.1 moles/mole CO also produces a reversal of zeta potential without affecting measured diameter, whilst at higher concentrations diameter almost doubles and zeta potential decreases but remains positive.

Zeta potential is a measure of surface charge and the observed results indicate that the peptides are spontaneously locating at the microemulsion droplet surface.

At low peptide concentrations (below 0.2 moles/mole CO) where diameter remains unchanged, the zeta potential increases produced by Peptides A and B are roughly equal whilst Peptide C has double the effect.

Peptides containing both anchors (Peptides A and C) produce increases in diameter at low concentrations (0.5 and 0.2 moles /mole CO respectively) whilst Peptide B with only one anchor had no effect at any concentration.

Similar effects were noted in native LDL where surfactant induced size increases were related to the molecular size of the lipophilic portion [13]. Absence of the cholesterol anchor does not appear to hinder peptide insertion into the particle since the zeta potentials obtained for Peptides A and B are similar. The increased peptide chain length in Peptide C also appears to have an effect on droplet diameter, which increases at lower concentrations than Peptide A.

The results suggest that the lipid anchors become buried in the microemulsion droplet's outer phospholipid layer whilst the relatively hydrophilic peptide remains on the outer surface.

In FIG. 9($a$) the effect of pH alterations on the measured zeta potential of various [Peptide A]-nLDL systems is presented. All exhibit a shift to negative values with increasing pH. [NP]-nLDL (without peptide) also exhibits this trend −10 mV over 3 pH units, which is related to changes in the ionic strength of the buffer due to pH adjustment with sodium hydroxide. At 0.532 moles Peptide A/mole CO the zeta potential change is −20 mV and at 0.106 moles Peptide A/mole CO −16 mV, both greater than the control.

At the extreme alkaline pH tested, all systems, with the exception of the highest Peptide A concentration, have similar zeta potential values. This indicates that ionisation of the peptide has been suppressed and the measured value is that of the microemulsion.

The results indicate that the peptide is exposed on the particle's surface. Results for three different n-LDL preparations at similar peptide concentrations are presented in FIG. 9($b$), all display the trend presented in FIG. 9($a$).

FIG. 9($b$) shows the effect of pH or, the measured Zeta Potential of various nLDL preparations.

In FIG. 10 results on the changes of the measured mean number diameter and zeta potential due to alterations in the microemulsion's surface lipid components are presented. The amphipathic lipid mixtures employed were at proportions relative to those found in native LDL [11].

Both Peptides A and B show a reversal of zeta potential with little change in diameter whilst Peptide C induces large alterations in both parameters. Within different nLDL systems only Peptide A exhibited a significant difference in zeta potential between the lipid formulations even although all have similar values before incorporation.

The results presented illustrate that completely synthetic analogue of LDL containing a receptor binding sequence from Apo-B100 can be prepared. The synthetic peptides employed incorporate into the surface of lipid microemulsions in a concentration dependent manner. The resultant particles have physiochemical properties which are comparable to native LDL, with slightly larger diameter but a controllable zeta potential.

EXAMPLE 3

Materials and Methods

B16 cells were obtained from the Dermatology Department of the Western Infirmary, Glasgow, United Kingdom.

Other materials, preparation of nLDL particles and analysis of cholesterol content follow the outlines as for Examples 1 and 2, above.

Incorporation of 14C-Cholesteryl Oleate

The required quantity of 14C-cholesteryl oleate (0.5 $\mu$Ci-/mmol CO, supplied dissolved in toluene) was mixed if required with ten times its volume of DMSO prior to addition to stirred nLDL heated at 55° C. in a water bath. After incubation for 5 hours the mixture was passed down a Sephadex G-25M gel exclusion chromatography column (bed volume 10 ml) eluted with PBS. Fractions (1 ml) were collected their absorbance (300 nm) and 14C-cholesteryl oleate activity measured. Labelled preparations were filter sterilised (0.2 $\mu$m) and stored at 4° C. under $N_2$ before use.

Tissue Culture

B16 cells were maintained in RPM: 1640 medium supplemented with 10% v/v FCS incubated at 37° C. in a 5% $CO_2$ in air atmosphere. Confluent cultures were trypsinised, harvested and re-seeded at a dilution of 1 in 20 in fresh medium.

Cell Binding Assays

B16 cells were harvested in the log growth phase, washed by centrifugation and re-seeded into 24 well plates $1 \times 10^5$ cells/ml in media containing 10 v/v DFCS. After overnight incubation the cells were cooled to 4° C. for 1 hour, the media aspirated and replaced with ice cold media containing 10% v/v DFCS, supplemented with 14C-nLDL at a cholesterol concentration of 0.08 mmol/l. Four replicate wells were used for each concentration. Cells were then incubated at 4° C. for 4 hours with occasional rocking, the media aspirated and cells washed three times with ice cold PBS/BSA buffer (2 mg/ml BSA in PBS) followed by two ten minute incubations with ice cold PBS/BSA. Three final washes with ice cold PBS were then conducted. The 14C-cholesteryl oleate was extracted with hexane/isocropanol for 30 minutes at room temperature, aspirated and then mixed with 3 ml of scintillation fluid prior to counting. Cellular protein left in the well after extraction was assayed using Peterson's modification of the Lowry method[14]. Sodium deoxycholate (1.5 mg/ml) was added to solubilise the protein, which was then precipitated by the addition of trichloroacetic acid (72% w/v), pelleted by centrifugation (5,000 rpm 10 minutes), the supernatant discarded and the pellet solubilised in Lowry reagent at room temperature for 20 minutes. Folin Ciocalteu's reagent was added, the solutions mixed and the colour allowed to develop for 30 minutes prior to absorbance measurements at 690 nm using a plate reader. A calibration curve was clotted from BSA standards ranging from 20 to 200 µg/ml.

Results and Discussion

To determine if nLDL would bind in a receptor dependent fashion, increasing amounts of radio-labelled [Peptide X]nLDL was added to B16 in vitro and the results are presented in FIG. 11. For four of the [Peptide X]nLDL particles (Peptide B, C, D and E) a saturable increase in total binding was obtained which is typical of receptor ligand interactions. [NP]nLDL (nLDL containing no peptide (NP)) also exhibited saturation binding whilst [Peptide A]nLDL provided a linear response at the concentrations tested. Clearly the choice of peptide incorporated in nLDL has a large effect on the interaction with B16 cells, since [Peptide D]nLDL had almost twice the binding of [Peptide C]nLDL at receptor saturation. Clearly the results indicate that interaction between [Peptide X]nLDL and B16 cells is occurring and that this is moderated by the incorporated peptide.

LDL receptor binding is comprised of two components, high affinity specific binding and non-specific binding (defined as ligand bound in the presence of an excess of unlabelled ligand) [16]. The former is routinely used for calculation of affinity constants and is determined by subtracting non-specific from total binding.

The non-specific and specific binding determined for various [Peptide X]nLDL preparations is presented in FIGS. 12(a) and 12(b). These results illustrate that for all the concentrations tested the specific binding of [Peptide B], [Peptide D] and [Peptide E]nLDL was higher than that obtained for either [NP], [Peptide C]nLDL. In addition [Peptide B], [Peptide D] and [Peptide E]nLDL exhibit higher specific than non-specific binding.

Double reciprocal plots are presented in FIG. 13 and the calculated constants in Table 1. For all preparations linear regression analysis provided correlation coefficients which were statistically significant (See Table 1). The remaining [Peptide X]nLDL preparations have a gradation of binding constants [Peptide E-]>[Peptide B]>[Peptide D]. Since [NP] nLDL provided a saturation binding curve it also provided a binding constant with a value very similar to [Peptide D]nLDL.

These results demonstrate that nLDL exhibits saturable binding kinetics with B16 cells in vitro at 4° C., with the extent of binding determined by the incorporated peptide's structure. An eleven amino acids peptide with two lipid anchors produces binding [Peptide A], however removal of the C-terminal cholesterol significantly improves performance [Peptide B]. A twenty two amino acid long peptide further enhances binding [Peptide C] and similarly removal of the cholesterol anchor results in further increases in binding competence [Peptide D]. This improvement can be modulated by using a random sequence [Peptide E] based on the amino acids present in the previous peptides. This strongly indicates that the measured binding is related to the peptide and its structure (length, lipid anchor and sequence) rather than some simple physical effect.

TABLE 1

Binding constants of [Peptide X] nLDL determined from double reciprocal plots of total binding

| Preparation | Kd (× $10^{-6}$ M) | Amax (× $10^{-5}$ M) |
|---|---|---|
| [NP] nLDL | 3.2 | 7.86 |
| [Peptide A] nLDL | * | * |
| [Peptide B] nLDL | 9.3 | 30.6 |
| [Peptide C] nLDL | 7.7 | 17.2 |
| [Peptide D] nLDL | 3.0 | 18.5 |
| [Peptide E] nLDL | 15.2 | 32.4 |

Values calculated using linear regression, all lines statistically significant p < 0.05.
* Not calculated since intercept positive.

EXAMPLE 4

Materials and Methods

Materials, preparation of microemulsion and of nLDL particles, and analysis of cholesterol content are as for Example 1, above with the exception that B16 cells are used in place of U937 cells.

Fluorescent Labelling of Microemulsion, nLDL

LDL, nLDL and microemulsion were labelled with DiO by a method modified from Stephan and Yuracheck [18] (as described hereinbelow). A fluorescent probe stock solution (3 mg/5 ml in DMSO) was added to LDL solution at a concentration of 300 µg/mg LDL protein or to microemulsion or nLDL suspension containing an equivalent concentration of cholesterol (1 mmol/l) in an identical volume. The lipid DiO mixture was incubated in the dark at 37° C. for five hours; then passed down a Sephadex G-25M column (bed volume 9.1 ml) eluted with PBS. The resulting labelled nLDL were filter sterilised (0.2 µm) and stored at 4° C. under $N_2$ before use. The DiO concentration of the microemulsions was determined using a fluorescence spectrophotometer (Perkin Elmer 203, Xenon Model 150 lamp) and excitation and emission wavelengths of 484 and 587 nm respectively. Samples of DiO labelled material (200 µl) were added to methanol (3 ml), fluorescence determined and concentration

Cell Culture

B16 cells in log phase were trypsinised and inoculated into 24 well plates at a concentration of $5 \times 10^4$ cells per well containing RPMI 1640 (1 ml) supplemented with 10% v/v FCS. Cells were left to grow 24 hours then serum starved in RPMI 1640 supplemented with 5% v/v DFCS for a further 24 hours. DiO labelled microemulsion and nLDL were filtered (0.2 μm) and added to wells at known concentrations. Plates were then incubated for three hours at either 4° C. to determine bound or 37° C. to determine cell associated DiO concentrations. Plates incubated at 4° C. were chilled tar 30 minutes prior to lipid addition. After incubation remaining media was aspirated, the cells carefully washed to prevent detachment then methanol (1 ml) added to each well and incubated at room temperature with gentle shaking for 30 minutes. The methanol extract was centrifuged at 5,000 rpm for 5 minutes, aspirated and added to methanol (2 ml) and the DiO concentration determined by fluorimetery as previously described. Cells incubated without DiO were also methanol extracted to account for auto-fluorescence. Three wells per plate were routinely assayed for protein concentration, by adding 2M NaOH and using Peterson's [14] modification of the Lowry method [15]. B16 cells are contact inhibited and were near confluency during the experimental procedure, the mean value from this determination was utilised. Specifically bound and associated DiO was determined by including a hundred fold excess concentration of non-labelled ligand in two wells for each concentration measured. Specific binding was calculated as total binding (without excess) less non-specific binding (with excess). Data was treated using a Scatchard and Double Reciprocal Analysis to calculate binding constants.

Results

To investigate if nLDL could be labelled for use in receptor binding studies, samples were chromatographed using a Sephadex G-25M column (PD-10). The fractions were monitored for DiO and cholesterol content and results are presented in Table 2.

To determine if the DiO was firmly bound to nLDL, samples were incubated with identical volumes of PBS containing Bovine Serum Albumin (BSA, 2 mg/ml) for 30 minutes at 37° C. and then chromatographed using a Sephacryl S-300 column. Over eighty percent of the fluorescence was associated with the particle (FIG. 14) and only a small amount co-eluted with the protein.

Carbocyanine dyes such as DiO are known to show little movement after insertion into a phospholipid layer especially if cholesterol is also present.

The data demonstrates that nLDL suspensions can be labelled with DiO using a modification of the method previously devised for LDL [17, 18].

Initial studies on the binding of DiO labelled nLDL to B16 cells were performed without an excess of unlabelled ligand. The original nLDL prepared was not concentrated enough to enable the sufficient excess (100 times labelled) to be added to small volume culture wells. [Peptide A]nLDL and microemulsion displayed similar binding profiles (FIG. 15), however [Peptide C]nLDL saturated at higher levels of added ligand. Total binding curves of DiO labelled nLDL to B16 cells at 4° C. appear to be dose dependent and saturable suggesting a receptor mediated interaction.

FIG. 16 shows the effect of increasing cholesterol concentration on the binding (specific, non-specific and total.) of labelled [Peptide A]nLDL and microemulsion to Bus cells; at 4° C. Both had similar total binding curves but microemulsion exhibited an increased non-specific component when compared with [Peptide A]nLDL. [Peptide A]nLDL non-specific binding although linear and therefore proportional to the amount added was greater than calculated specific binding. [Peptide A]nLDL specific binding appears to be concentration dependent but at the concentrations examined was not saturable.

The amount of nLDL internalised in three hours at 37° C. can be calculated by subtracting total bound from total cell associated (FIG. 17). [Peptide A]nLDL produces a linear dose response for all three parameters over a cholesterol range of 0 to 25 μmol/l, suggesting that even the highest concentration of [Peptide A]nLDL was not saturating the receptor dependent uptake.

These results show that [Peptide A]nLDL can readily bind to LDL receptors.

Receptor binding constants were calculated from Scatchard and Double reciprocal plots (FIGS. 18(a) and 18(b) and are shown in Table 3. Both types of analysis resulted in much higher association constants for [Peptide A]nLDL and [Peptide C]nLDL when compared with microemulsion.

The results highlight the differences between particle with and without peptide and between the peptides. Specific binding appears to be conferred by the presence of the peptide and the degree of binding is controlled by peptide structure.

The results indicate that the inclusion of an amphipathic peptide containing the ApoB receptor sequence onto nLDL particles confers high affinity binding to a cell surface receptor and that binding affinity is influenced by peptide length. Doubling peptide lengths from 11 to 22 amino acids almost doubles the measured affinity.

This result coupled with the data presented in Example 1 indicates that [Peptide X]nLDL particles interact with the Low Density Lipoprotein receptor on B16 cells. This interaction is controlled by the amphipathic peptide's over-all length and the number of lipophilic anchors; two anchors produce a lower binding than a single one.

TABLE 2

Recovery of cholesterol and DiO from PD-10 elutions of LDL and nLDL.

|  | Starting Concentration nLDL | Total Recovered | Percentage Recovered nLDL |
|---|---|---|---|
| Cholesterol | 2.8 μmol | 2.4 μmol | 96% |
| DiO | 600 μg | 124.6 μg | 21% |

TABLE 3

Receptor Binding Constants determined from Scatchard and Double Reciprocal Analysis.

| | Scatchard | | | Double Reciprocal | | |
|---|---|---|---|---|---|---|
| Sample | Kd | k | Bmax | Kd | k | Bmax |
| Microemulsion | 1.28 | 0.78 | 0.028 | 6.92 | 0.14 | 0.092 |
| [PeptideA]nLDL | 0.53 | 1.9 | 0.026 | 1.17 | 0.85 | 0.037 |
| [PeptideB]nLDL | 0.37 | 2.7 | 0.081 | 0.70 | 1.43 | 0.093 |

EXAMPLE 5

Materials, and methods of preparation of nLDL particles, analysis of cholesterol content, cell culture and growth or proliferation assay are as described for Example 1. Photon correlation spectroscopy and zeta potential measurement are as described in Example 2.

Results

Several studies have suggested that estrogens exert a hypolipidaemic effect via upregulation of LDL receptor numbers and subsequent enhanced plasma LDL clearance [19]. If nLDL induced proliferation of U937 occurs via the LDL receptor the addition of estrogen to the media should enhance this effect. The results of estrogen treatment on induced proliferation is presented in FIG. 19. Estrogen has no effect on control systems without peptide but produces a dramatic increase in proliferation for [Peptide A]nLDL and [Peptide B]nLDL at similar peptide concentrations. The estrogen stimulated [Peptide B]nLDL proliferation at higher peptide concentrations is less and is completely lost at the highest value tested. The significantly increased U937 proliferation achieved suggests that these systems do utilise the LDL receptor pathway. The lack of estrogen stimulation of [NP]nLDL indicates that the effect cannot be ascribed to increased phagocytosis or some other similar non-specific mechanism.

Estrogenic stimulation of proliferation is further indication that nLDL uptake is via the LDL receptor pathway. nLDL systems are indicated as being useful as controllable LDL substitutes for application to drug targeting tasks.

References

1. Ginsburg, G. S., Small, D. M. & Atkinson, D. J. Biol. Chem. 257 (14), 8216–8227 (1982).
2. Knott, T. J., et al. Nature 323, 734–738 (1986).
3. Frostegård, J., Hamsten, A., Gidlund, M. & Nilsson, J. J. Lipid Res. 31, 37–44 (1990).
4. Schewem C. K., et al. Eur J Clin Invest- 24, 36–41 (1994).
5. Sells, T. & Barakat, H. Med Sci Res 22, 5–6 (1994).
6. Rothblat, G. H., Arbogast, L. Y., Ouellette, L. & Howard, B. V. In Vitro 12, 554–557 (1976).
7. Van den Broek, A. J. C. M., et al. Clin. Chem. 40, 395–399 (1994).
8. Owens, M. D. & Halbert, G. W. Eur J Pharm Biopharm (1995) 41(2): p120–126.
9. Allain, C. C. Clin. Chem. 20, 470–475 (1974).
10. Sundström, C. & Nilsson, K. Int. J. Cancer 17, 565–577 (1976).
11. Skipaki, V. P. et al. Biochem J. 104: pp 340–352 (1967).
12. Washington, C. Ellis Harwood Series in Pharmaceutical Technology, ed. M. H. Rubinstein (1992), London: Ellis Harwood 243.
13. Tucker, I. G. and A. T. Florence J. Pharm. Pharmacol., (1983) 35: p705–711.
14. Peterson, G. A. Anal. Biochem., (1977) 83: pp 346–356.
15. Lowry, O. H. et al. J. Biol. Chem., (1951) 193: pp 265–275.
16. Brown, M. S. and Goldstein J. L., Proc. Natt. Acad. Sci. USA, (1974) 71, pp 788–792.
17. Pitas R. E., et al. Arterioscherosis, (1981) 1 (3) pp 177–185.
16. Stephan, Z. E. and Yurachek E. C., J. Lipid Res. (1993) 34 pp 325–330.
19. Srivastava, R. A. K. et al. Eur. J. Biochem., (1994) 219 (3): p1087

What is claimed is:

1. A non-naturally occurring, receptor competent low density lipoprotein particle comprising
   at least one peptide component covalently bonded to
   at least lipophilic substituent selected from the group consisting of
      cholesterol, retinoic acid, and $C_{10}$–$C_{22}$ fatty acids,
   wherein the at least one peptide component comprises at least a binding site for an Apo B protein receptor, and
   wherein the at least one peptide component is from 8 to 500 amino acid residues long.

2. A particle according to claim 1 wherein the at least one peptide component comprises at least a binding site for an Apo B protein receptor made up of amino acid residues selected from the group consisting of lysine, alanine, glutamine, tyrosine, asparagine, histidine, arsinine, threonine, leucine and glycine and analogues thereof.

3. The particle according to claim 1 wherein the at least one peptide component is from 8 to 200 amino acid residues long.

4. The particle according to claim 3 wherein the at least one peptide component is from 8 to 50 amino acid residues long.

5. The particle according to claim 4 wherein the at least one peptide component is from 9 to 30 amino acid residues long.

6. A particle according to claim 1 wherein the peptide component further comprises a hydrophilic substituent selected from the group consisting of hydroxyl, carboxyl and amino groups.

7. A particle according to claim 1 wherein the binding sequence of the peptide component has at least a 70% amino acid identity to an Apo B protein binding sequence.

8. A particle according to claim 7 wherein the binding sequence of the peptide component has at least a 80% amino acid identity to an Apo B protein binding sequence.

9. A particle according to claim 8 wherein the binding sequence of the peptide component has at least a 90% amino acid identity to an Apo B protein binding sequence.

10. A pharmaceutical formulation comprising a non-naturally occurring receptor competent low density particle according to claim 1 together with a pharmaceutically acceptable carrier.

11. A non-naturally occurring, receptor competent low density lipoprotein particle comprising
    at least one peptide component covalently bonded to
    at least one lipophilic substituent selected from the group consisting of
       cholesterol, retinoic acid, and $C_{10}$–$C_{22}$ fatty acids,
    wherein the at least one peptide component comprises at least one binding site selected from the group consisting of
    (1) Lys Ala Glu Tyr Lys Lys Asn Lys His Arg His (SEQ ID NO: 1) or a dimer thereof; and
    (2) Thr Thr Arg Leu Thr Arg Lys Arg Gly Leu Lys (SEQ ID NO: 2) or a dimer thereof.

12. A non-naturally occurring, receptor competent low density lipoprotein particle comprising
    at least one peptide component covalently bonded to
    at least one lipophilic substituent selected from the group consisting of
       cholesterol, retinoic acid, and $C_{10}$–$C_{22}$ fatty acids,
    wherein the peptide component is selected from the group consisting of peptide A (SEQ ID NO: 3), peptide B (SEQ ID NO: 4), peptide C (SEQ ID NO: 5), peptide D (SEQ ID NO: 6), and peptide E (SEQ ID NO: 7).

* * * * *